(12) United States Patent
Clague et al.

(10) Patent No.: US 12,097,115 B2
(45) Date of Patent: Sep. 24, 2024

(54) PROSTHESIS WITH ANTI-PARAVALVULAR LEAKAGE COMPONENT INCLUDING A ONE-WAY VALVE

(71) Applicant: Medtronic, Inc., Minneapolis, MN (US)

(72) Inventors: Cynthia Clague, Minnetonka, MN (US); Ana Menk, Shoreview, MN (US); Timothy Petersen, Fridley, MN (US); Paul Rothstein, Elk River, MN (US); Stephen Roller, Rockville, MD (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/154,100

(22) Filed: Jan. 13, 2023

(65) Prior Publication Data

US 2023/0149160 A1 May 18, 2023

Related U.S. Application Data

(62) Division of application No. 16/579,941, filed on Sep. 24, 2019, now Pat. No. 11,583,397.

(51) Int. Cl.
*A61F 2/24* (2006.01)
(52) U.S. Cl.
CPC .......... *A61F 2/2418* (2013.01); *A61F 2/2412* (2013.01); *A61F 2/2433* (2013.01);
(Continued)
(58) Field of Classification Search
CPC ........ A61F 2002/077; A61F 2250/0003; A61F 2/24–2424; A61F 2/2475
See application file for complete search history.

(56) References Cited

U.S. PATENT DOCUMENTS 5,335,398 A  8/1994 Schottker et al.
5,571,175 A  11/1996 Vanney et al.
(Continued)

FOREIGN PATENT DOCUMENTS

EP   0537487 B1   4/1993
WO   2009/094501 A1   7/2009
(Continued)

OTHER PUBLICATIONS

Machine translation of WO 2014056701 A1, from European Patent Office website, 16 pages, accessed Jan. 26, 2024. https://translationportal.epo.org/emtp/translate/?ACTION=description-retrieval&COUNTRY=WO&ENGINE=google&FORMAT=docdb&KIND=A1&LOCALE=en_EP&NUMBER=2014056701&SRCLANG=fr&TRGLANG=en (Year: 2014).*

(Continued)

*Primary Examiner* — Rebecca S Preston
(74) *Attorney, Agent, or Firm* — Medler Ferro Woodhouse & Mills PLLC

(57) ABSTRACT

A transcatheter prosthesis includes a stent, a prosthetic valve component, and an anti-paravalvular leakage component. The anti-paravalvular leakage component is coupled to the stent and includes an inner skirt, an outer wrap, a cavity, an opening, and a one-way valve. The inner skirt is disposed on an inner surface of the stent and has an inflow end and a downstream end. The outer wrap is disposed around an outer surface of the stent and has an inflow end coupled to the inflow end of the inner skirt and a downstream end. The cavity is formed between an outer surface of the inner skirt and an inner surface of the outer wrap. An opening is disposed between the inner skirt and the outer wrap. The one-way valve includes a flap at the opening configured to open to allow blood flow into the cavity but prevent blood flow out of the cavity.

15 Claims, 18 Drawing Sheets

(52) U.S. Cl.
CPC ..... *A61F 2/2463* (2013.01); *A61F 2210/0014* (2013.01); *A61F 2250/0003* (2013.01); *A61F 2250/0069* (2013.01)

(56) References Cited

U.S. PATENT DOCUMENTS

| | | |
|---|---|---|
| 7,276,078 B2 | 10/2007 | Spenser et al. |
| 7,331,991 B2 | 2/2008 | Kheradvar et al. |
| 7,628,805 B2 | 12/2009 | Spenser et al. |
| 7,708,775 B2 | 5/2010 | Rowe et al. |
| 8,002,825 B2 | 8/2011 | Letac et al. |
| 8,182,528 B2 | 5/2012 | Salahieh et al. |
| 8,231,670 B2 | 7/2012 | Salahieh et al. |
| 8,449,599 B2 | 5/2013 | Chau et al. |
| 8,603,160 B2 | 12/2013 | Salahieh et al. |
| 8,623,078 B2 | 1/2014 | Salahieh et al. |
| 8,628,566 B2 | 1/2014 | Eberhardt et al. |
| 8,641,757 B2 | 2/2014 | Pintor et al. |
| 8,668,733 B2 | 3/2014 | Salahieh et al. |
| 8,673,000 B2 | 3/2014 | Tabor et al. |
| 8,734,484 B2 | 5/2014 | Ahlberg et al. |
| 8,795,357 B2 | 8/2014 | Yohanan et al. |
| 8,801,706 B2 | 8/2014 | Rothstein et al. |
| 8,802,356 B2 | 8/2014 | Braido et al. |
| 8,808,356 B2 | 8/2014 | Braido et al. |
| 2003/0199963 A1 | 10/2003 | Tower et al. |
| 2003/0199971 A1 | 10/2003 | Tower et al. |
| 2004/0030381 A1 | 2/2004 | Shu |
| 2004/0111111 A1 | 6/2004 | Lin |
| 2004/0122514 A1 | 6/2004 | Fogarty et al. |
| 2006/0004442 A1 | 1/2006 | Spenser et al. |
| 2007/0270944 A1 | 11/2007 | Bergheim et al. |
| 2007/0293944 A1 | 12/2007 | Spenser |
| 2008/0243245 A1 | 10/2008 | Thambar |
| 2009/0099653 A1 | 4/2009 | Suri et al. |
| 2009/0112311 A1 | 4/2009 | Miles et al. |
| 2009/0192591 A1 | 7/2009 | Ryan et al. |
| 2010/0036479 A1 | 2/2010 | Hill et al. |
| 2010/0168839 A1 | 7/2010 | Braido et al. |
| 2010/0168844 A1 | 7/2010 | Toomes et al. |
| 2010/0198238 A1 | 8/2010 | Sorajja |
| 2010/0280589 A1 | 11/2010 | Styrc |
| 2011/0054466 A1 | 3/2011 | Rothstein et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0245911 A1 | 10/2011 | Quill et al. |
| 2011/0257721 A1 | 10/2011 | Tabor |
| 2011/0257725 A1 | 10/2011 | Argentine |
| 2011/0264206 A1 | 10/2011 | Tabor |
| 2012/0022633 A1 | 1/2012 | Olson et al. |
| 2012/0041549 A1 | 2/2012 | Salahieh et al. |
| 2012/0041550 A1 | 2/2012 | Salahieh et al. |
| 2013/0190857 A1 | 7/2013 | Mitra et al. |
| 2013/0304200 A1 | 11/2013 | McLean et al. |
| 2013/0331929 A1 | 12/2013 | Mitra et al. |
| 2014/0046426 A1 | 2/2014 | Kovalsky |
| 2014/0114402 A1 | 4/2014 | Ahlberg et al. |
| 2014/0114406 A1 | 4/2014 | Salahieh et al. |
| 2014/0194975 A1 | 7/2014 | Quill et al. |
| 2014/0194981 A1 | 7/2014 | Menk et al. |
| 2014/0222144 A1 | 8/2014 | Eberhardt et al. |
| 2014/0236287 A1 | 8/2014 | Clague et al. |
| 2014/0243966 A1 | 8/2014 | Garde et al. |
| 2014/0243969 A1 | 8/2014 | Venkatasubramanian et al. |
| 2014/0257475 A1 | 9/2014 | Gross et al. |
| 2014/0277388 A1 | 9/2014 | Skemp |
| 2014/0277413 A1 | 9/2014 | Richter et al. |
| 2014/0277417 A1 | 9/2014 | Schraut et al. |
| 2014/0277419 A1 | 9/2014 | Garde et al. |
| 2014/0277423 A1 | 9/2014 | Alkhatib et al. |
| 2014/0277424 A1 | 9/2014 | Oslund |
| 2014/0277425 A1 | 9/2014 | Dakin |
| 2014/0277426 A1 | 9/2014 | Dakin et al. |
| 2014/0277428 A1 | 9/2014 | Skemp et al. |
| 2014/0324164 A1 | 10/2014 | Gross et al. |
| 2016/0038281 A1* | 2/2016 | Delaloye ............... A61F 2/2418 623/2.18 |
| 2016/0354201 A1 | 12/2016 | Keogh |
| 2017/0360559 A1 | 12/2017 | Mayer |
| 2018/0028310 A1 | 2/2018 | Gurovich et al. |
| 2018/0185132 A1 | 7/2018 | Baxter et al. |
| 2019/0053894 A1 | 2/2019 | Levi et al. |

FOREIGN PATENT DOCUMENTS

| | | | |
|---|---|---|---|
| WO | 2011/051043 A1 | 5/2011 | |
| WO | 2013/033791 A1 | 3/2013 | |
| WO | 2013/037519 A1 | 3/2013 | |
| WO | 2013/059747 A1 | 4/2013 | |
| WO | WO-2014056701 A1 * | 4/2014 | ........... A61F 2/2418 |
| WO | 2014/072439 A1 | 5/2014 | |

OTHER PUBLICATIONS

International Search Report and Written Opinion in corresponding PCT Application No. PCT/US2020/052388, mailed Jan. 22, 2021.

* cited by examiner

PROSTHESIS WITH ANTI-PARAVALVULAR LEAKAGE COMPONENT INCLUDING A ONE-WAY VALVE

CROSS-REFERENCE TO RELATED APPLICATIONS

This application is a division of U.S. application Ser. No. 16/579,941, filed Sep. 24, 2019, the contents of which are incorporated by reference herein in their entirety.

FIELD OF THE INVENTION

The invention relates generally to prostheses for intervascular delivery. More particularly, the present invention relates to valve prostheses with an anti-paravalvular leakage component to assist in the prevention of paravalvular leakage at the deployed valve prosthesis.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To ensure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream direction.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such valve prostheses can be percutaneously delivered while in a low-profile or radially compressed configuration so that the valve prosthesis can be advanced through the patient's vasculature and deployed at the site of the diseased heart valve through catheter-based systems. Once positioned at the treatment site, the valve prosthesis can be expanded to engage tissue at the diseased heart valve region to, for instance, hold the valve prosthesis in position.

However, in some patients, the valve prosthesis may not perform as desired following implantation. For example, in some patients, the radial expansion of the valve prosthesis may not conform to the shape of the wall of the native valve. This situation may occur when the wall of the native valve is misshapen or heavily calcified. In such cases where the valve prosthesis is not fully coapted to the wall of the native valve, paravalvular leakage (PVL) may occur between the valve prosthesis and the wall of the native valve, and high levels of PVL are associated with increased mortality.

Accordingly, there is a need for systems and components to improve sealing of a valve prosthesis to a native valve wall, while maintaining a small compressed profile for percutaneous delivery.

BRIEF SUMMARY OF THE INVENTION

Embodiments hereof are directed to a transcatheter valve prosthesis including a stent, a prosthetic valve component, and an anti-paravalvular leakage component. The stent includes a radially compressed configuration for delivery within a vasculature and a radially expanded configuration for deployment within a native heart valve. The prosthetic valve component is disposed within and coupled to the stent. The anti-paravalvular leakage component is coupled to the stent. The anti-paravalvular leakage component includes an inner skirt, an outer wrap, a cavity, an opening, and a one-way valve. The inner skirt has an inflow end and an opposing downstream end and is disposed on an inner surface of the stent. The inner skirt is formed of a flexible material. The outer wrap has an inflow end coupled to the inflow end of the inner skirt and an opposing downstream end. The outer wrap is disposed around an outer surface of the stent and is formed of a flexible material. The cavity is formed between an outer surface of the inner skirt and an inner surface of the outer wrap. An opening is disposed between the inner skirt and the outer wrap at the corresponding inflow ends of the inner skirt and the outer wrap and/or the corresponding downstream ends of the inner skirt and the outer wrap. The one-way valve includes a flap disposed at the opening and between the outer surface of the stent and an inner surface of the outer wrap. The flap is formed of a flexible material and is configured to open to allow blood flow into the cavity but prevent blood flow out of the cavity.

Embodiments hereof are also directed to a transcatheter valve prosthesis including a stent, a prosthetic valve component, and an anti-paravalvular leakage component. The stent includes a radially compressed configuration for delivery within a vasculature and a radially expanded configuration for deployment within a native heart valve. The prosthetic valve component is disposed within and coupled to the stent. The anti-paravalvular leakage component is coupled to the stent. The anti-paravalvular leakage component includes an inner skirt, an outer wrap, a cavity, an opening, and a one-way duckbill valve. The inner skirt is formed of a flexible material and has an inflow end and an opposing downstream end. The inner skirt is disposed on an inner surface of the stent. The outer wrap is disposed around an outer surface of the stent and has an inflow end coupled to the inflow end of the inner skirt and an opposing downstream end. The outer wrap and is formed of a flexible material. The cavity is formed between an outer surface of the inner skirt and an inner surface of the outer wrap. An opening is disposed between the inner skirt and the outer wrap at the corresponding inflow ends of the inner skirt and the outer wrap and/or the corresponding downstream ends of the inner skirt and the outer wrap. The one-way duckbill valve includes an inner flap and an outer flap. The inner flap is disposed adjacent the opening and between the outer surface of the stent and an inner surface of the outer wrap. The outer flap is disposed at the opening and between the outer surface of the stent and an inner surface of the outer wrap. The inner and the outer flaps are each formed of a flexible material and are configured to open to allow blood flow into the cavity but prevent blood flow out of the cavity.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to blood flow. "Distal" and "distally" refer to positions in the downstream direction with respect to the direction of blood flow. "Proximal" and "proximally" refer to positions in an upstream direction with respect to the direction of blood flow.

The following detailed description is merely exemplary in nature and is not intended to limit the invention or the application and uses of the invention. Although the description of embodiments hereof are in the context of treatment of a native heart valve such as an aortic valve, the invention may also be used at other heart valve locations and in any other body passageways where it is deemed useful. Furthermore, there is no intention to be bound by any expressed or implied theory presented in the preceding technical field, background, brief summary or the following detailed description.

A transcatheter valve prosthesis in accordance with embodiments hereof includes a valve prosthesis) and an anti-paravalvular leakage (PVL) component. The anti-PVL component is generally formed of tissue and is highly compressible to a low profile for transcatheter delivery to a desired treatment location. The anti-PVL component is generally disposed at the inflow end of the transcatheter valve prosthesis and includes an inner layer or skirt, and an outer layer or wrap forming a cavity between the outer and inner layers accessible via a one-way valve allowing blood to flow into the cavity but not out of the cavity. When the cavity is filled with blood, the outer layer distends or expands radially outward to fill in gaps along the perimeter of the transcatheter valve prosthesis and a native anatomy when the transcatheter valve prosthesis is in the radially expanded configuration at the desired treatment location. Once the cavity is filled with blood, the anti-PVL component is dynamically stable, and the pooled blood within the anti-PVL component will clot.

Figure 1:
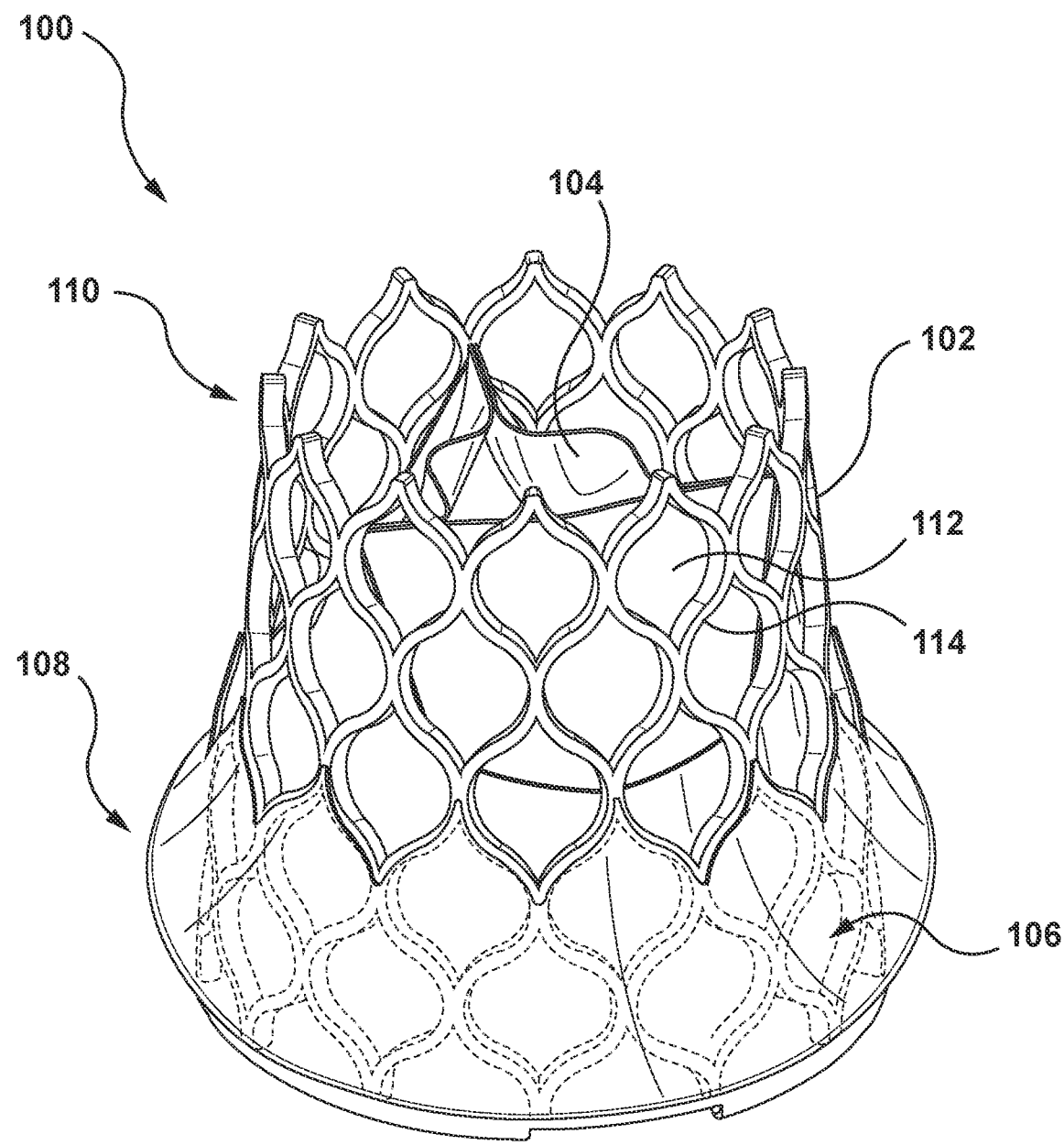
FIG. 1 is a perspective illustration of a prosthesis with an anti-PVL component according to an embodiment hereof.

In an embodiment shown in FIG. 1, a transcatheter valve prosthesis 100 (hereafter referred to as prosthesis 100 for simplicity) includes a generally tubular stent 102, a prosthetic valve component 104 (hereafter referred to as valve component 104 for simplicity), and an anti-paravalvular leakage component 106 (hereafter referred to as anti-PVL component 106 for simplicity). The prosthesis 100 is configured to replace and replicate the function of a native heart valve.

In embodiments hereof, the stent 102 has a radially compressed configuration for delivery and a radially expanded configuration for deployment within a native heart valve. In some embodiments, the stent 102 is a self-expanding frame configured to return to a radially expanded configuration from a radially compressed configuration. In other embodiments, the stent 102 may be a balloon expandable frame that plastically deforms to maintain a radially expanded configuration when expanded by a balloon or other expansion device from a radially compressed configuration. The stent 102 includes an inflow section 108 and an outflow section 110, as shown in FIG. 1. The stent 102 further includes a plurality of cells 112 formed by a plurality of struts 114 arranged relative to each other to provide a desired compressibility and strength to the prosthesis 100. The cells 112 may have sizes that vary along the length of the stent 102. The stent 102 may be formed of various materials including, but not limited to stainless steel, nickel-titanium alloys (e.g. NITINOL), or other suitable materials. "Self-expanding" as used herein means that a structure has been formed or processed to have a mechanical or shape memory to return to the radially expanded configuration. Mechanical or shape memory may be imparted to the structure that forms the stent 102 using techniques understood in the art. The stent 102 may assume different forms and features described, for example, but not by way of limitation, in U.S. Pat. No. 7,740,655 to Birdsall, and U.S. Pat. No. 8,128,710 to Nguyen et al., each of which is incorporated by reference herein in its entirety.

Figure 2:
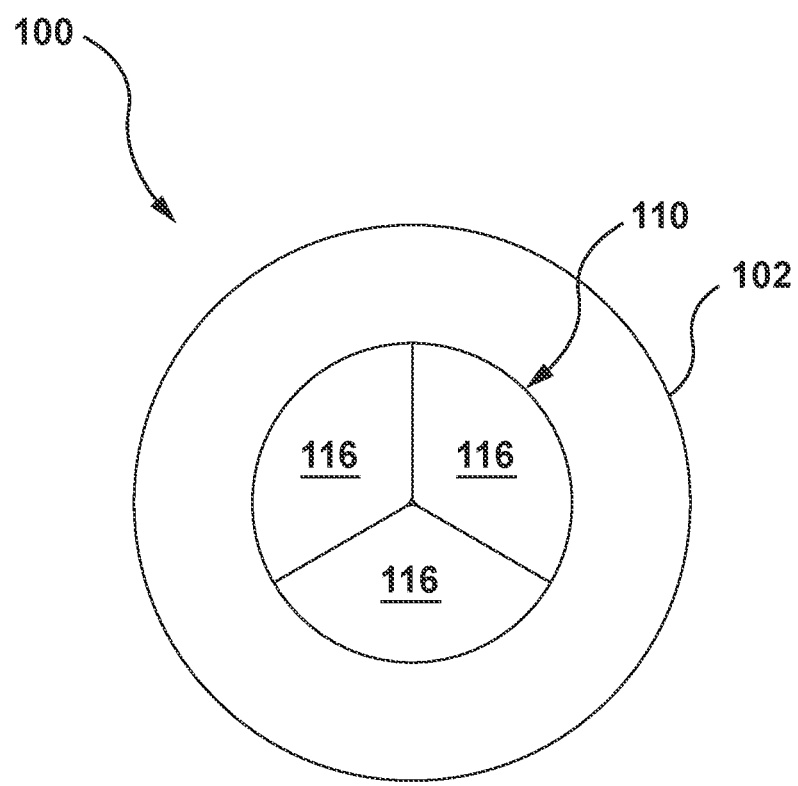
FIG. 2 is a top illustration of the prosthesis of FIG. 1.

In embodiments hereof, the valve component 104 is disposed within and secured to the tubular stent 102. The valve component 104 may comprises a plurality of individual leaflets 116 assembled to simulate the leaflets of a native valve, as best shown in FIG. 2. Adjoining pairs of the leaflets 116 are attached to one another at their lateral ends to form commissures (not shown in FIG. 2), with free edges of the leaflets 116 forming coapted edges that meet in an area of coaptation, as described in U.S. Pat. No. 8,128,710 to Nguyen et al., previously incorporated by reference herein in its entirety. The components of the valve component 104 are formed of materials such as, but not limited to mammalian tissue such as porcine, equine or bovine pericardium, or a synthetic or polymeric material.

Figure 3:
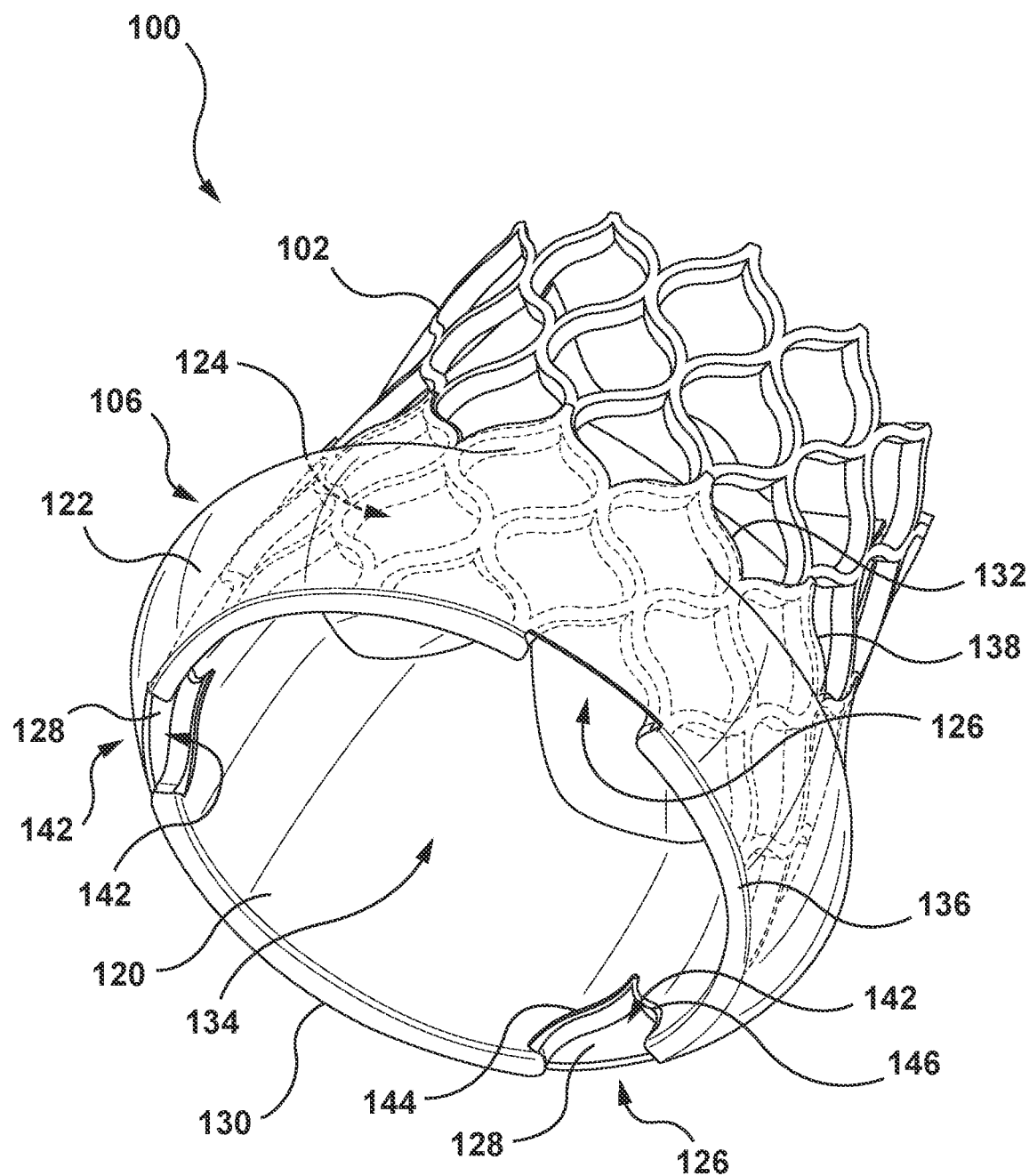
FIG. 3 is a perspective illustration of an inflow portion of the prosthesis of FIG. 1.

The anti-PVL component 106 is coupled to the tubular stent 102 and includes an inner layer or skirt 120, an outer layer or wrap 122, a cavity 124 (obscured from view by the outer wrap 122 in FIG. 3), a plurality of openings 126, and a plurality of one-way valves 128 (hereafter referred to as valves 128 for simplicity), as best shown in FIG. 3. The anti-PVL component 106 is configured to fill in and seal gaps between the prosthesis 100 and the native anatomy when the stent 102 is in the radially expanded configuration at a desired treatment location and the outer wrap 122 of the anti-PVL component 106 is in an expanded state.

The inner skirt 120 includes a generally circular inflow end 130, and a downstream end 132 opposite the inflow end 130, as shown in FIG. 3. The inner skirt 120 is disposed on an inner surface of the stent 102. The downstream end 132 is coupled to the stent 102 and to the outer perimeter of the leaflets 116. The inflow end 130 is coupled to an inflow end 136 of the outer wrap 122 and the stent 102 as described below. The inner skirt 120 is formed of a flexible material such as, but not limited to polyester, nylon, expanded polytetrafluoroethylene (ePTFE), natural tissue (e.g. porcine, equine, or bovine pericardium), or other materials suitable for the purposes described herein. The inflow end 130 of the inner skirt 120 may be coupled to the downstream end 136 of the outer wrap 122 and the stent 102 by methods such as, but not limited to sutures, laser or ultrasonic welding, or outer suitable methods. Similarly, the downstream end 132 of the inner skirt 120 may be coupled to the stent 102 and leaflets 116 in a manner such as, but not limited to sutures, laser or ultrasonic welding, or outer suitable methods. The inner skirt 120 is attached to the stent 102 in a "tight" manner such that the inner skirt 120 does not expand inwardly when the cavity 124 is filled, as described in more detail below. By a "tight" manner, it is meant that an outer surface of the inner skirt 120 abuts an inner surface of the stent 102 along the length of the inner skirt 120. This arrangement can be accomplished by having little or no slack in the inner skirt 120 between the downstream end 132 attachment and the inflow end 130 attachment. It can also be accomplished by having multiple attachments between the inner skirt 120 and the stent 102 along the length of the inner skirt 120 between the inflow end 130 and the downstream end 132. Other ways to maintain the inner skirt tight against the inner surface of the stent 102 may also be used, as would be understood by those skilled in the art.

Also shown in FIG. 3, the outer wrap 122 includes the generally circular inflow end 136 and an opposing downstream end 138. The outer wrap 122 further includes a radially contracted state when blood is not received within the cavity 124 and the radially expanded state when blood is received within the cavity 124 and distends or radially expands the outer wrap 122. The outer wrap 122 is disposed around an outer surface of the tubular stent 102. The inflow end 132 of the outer wrap 122 is coupled to the inflow end 130 of the inner wrap 120 as described below. The downstream end 138 of the outer wrap 122 is coupled to the stent 102. The outer wrap 122 is sized such that the outer wrap 122 has sufficient material available or slack to distend radially outward to the radially expanded state. The outer wrap 122 may be formed of a flexible and expandable material such as, but not limited to silicone, chronoprene, urethane, nylon, natural tissue (e.g. porcine, equine, or bovine pericardium), or other materials suitable for the purposes described herein. Non-expandable materials may also be used and may be attached more loosely to the stent 102 than an expandable material would be. The inflow end 132 of the outer wrap may be coupled to the inflow end 130 of the inner skirt 122 and the tubular stent 102 by methods such as, but not limited to sutures, laser or ultrasonic welding, or outer suitable methods. The downstream end 132 of the outer wrap 122 may be coupled to the tubular stent 102 in a manner such as, but not limited to sutures, laser or ultrasonic welding, or outer suitable methods.

The cavity 124 is thus formed between the between an outer surface of the inner skirt 120 and an inner surface of the outer wrap 122. The cavity 124 is configured to receive blood through the plurality of valves 128 at the plurality of openings 126, as shown in FIG. 3.

As also shown in FIG. 3, the anti-PVL component 106 includes the plurality of openings 126 between the inner skirt 120 and the corresponding plurality of valves 128. In an embodiment, each opening 126 is disposed at the inflow ends 130, 136 of the inner skirt 120 and the outer wrap 122, respectively, between the inner skirt 120 and the outer wrap 122. Each opening 126 is configured to allow blood flow to the corresponding valve 128 of the anti-PVL component 106. Each opening 126 is formed by a cut-out portion 142 of the inner skirt 120. A first edge 144 and a second edge 146 of each cutout portion of the inner skirt 120 is coupled to the inner surface of the stent 102 such that each cut-out portion 142 of the inner skirt 120 is disposed downstream of the inflow end 136 of the outer wrap 122. Thus the first and second edges 144, 146 of the cut-out portion 142 follow the shape of a cell of the stent 102 and the first and second edges 144, 146 are attached to the inner surface of the stent 102 to prevent blood flow between the stent 102 and the first and second edges 144, 146. Thus, each opening 126 is defined by a portion of the tubular stent 102 at the cut-out portion 142 of the inner skirt 120, the inflow end 130 of the inner skirt 120 at the cut-out portion 142, and an inner surface of the outer wrap 122 at the cut-out portion 142. While shown as three (3) openings spaced equally at the inflow ends 130, 132 of the inner skirt 120 and the outer wrap 122, respectively, this is not meant to be limiting, and more or fewer opening 126 may be utilized and disposed with any suitable spacing at the inflow ends 130, 136 and/or the downstream ends 132, 138 of the inner skirt 120 and the outer wrap 122.

Figure 4:
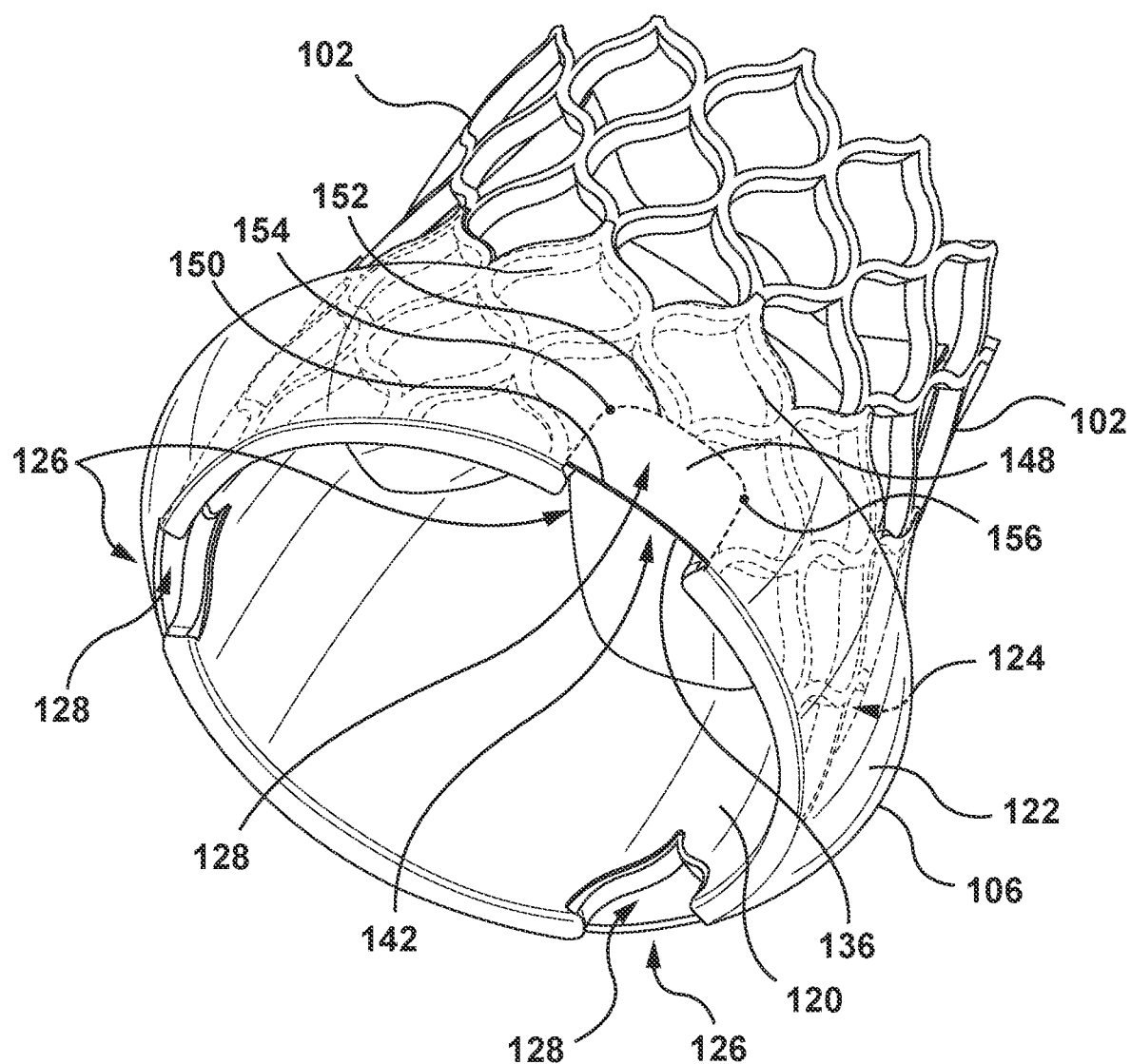
FIG. 4 is another perspective illustration of the inflow portion of the prosthesis of FIG. 1, with the structure within an anti-PVL component is shown in phantom.
Figure 5:
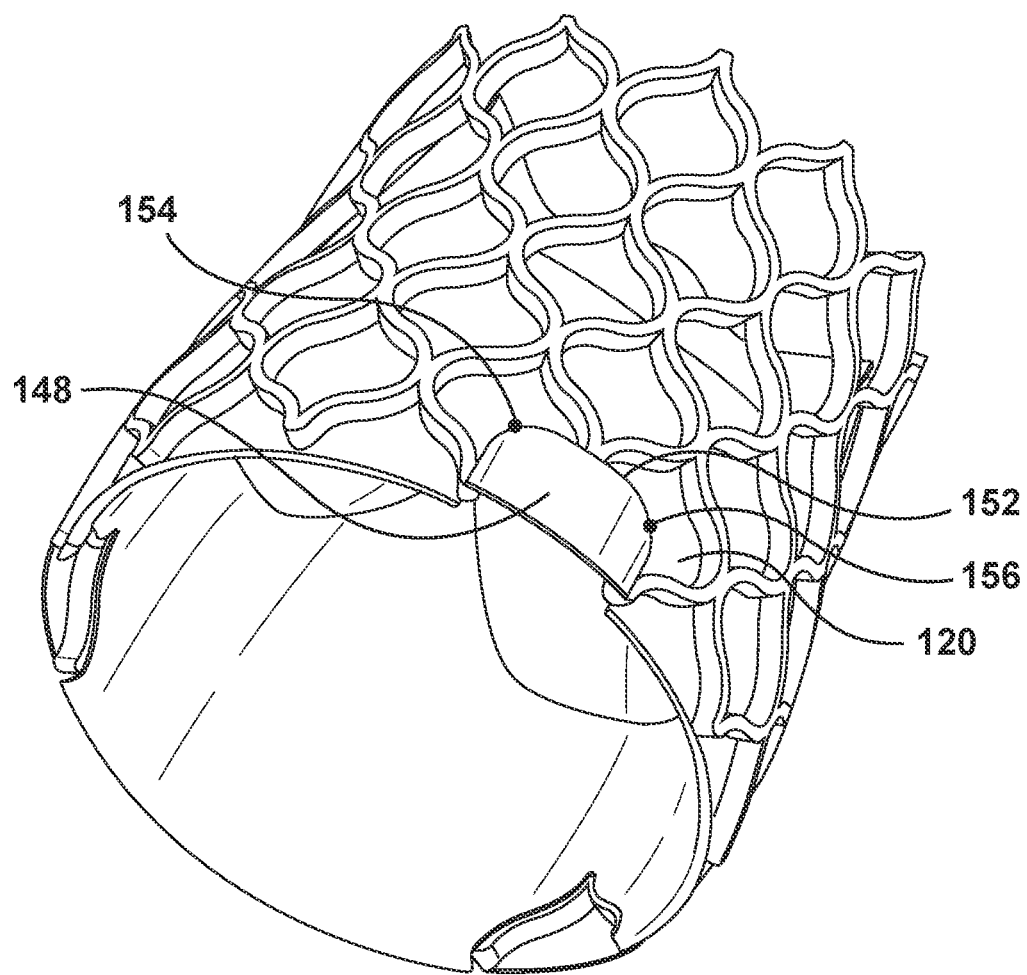
FIG. 5 is a perspective illustration of the inflow portion of the prosthesis of FIG. 1, wherein a flap of a valve is visible and the outer wrap has been removed for clarity.

Referring next to FIGS. 4 and 5, each valve 128 of the plurality of valves 128 includes a flap 148. Each flap 148 is a generally rectangular shape and is configured to open to allow blood flow into the cavity 124 of the anti-PVL component 106 and further configured to close to prevent blood flow from out of the cavity 124. The flap 148 of each valve 128 is disposed at a corresponding opening 126 of the inner skirt 120, between the outer surface of the stent 102 and the inner surface of the outer wrap 122. Each flap 148 includes a first end 150 coupled to the inflow end 136 of the outer wrap 122 at the cut-out portion 142 of the corresponding opening 126 and a second end 152. Each flap 148 is sized to cover the cut-out portion 142. A portion of the flap 148 spaced from the first end 150 extends over the struts 114 of the stent 102 defining the opening 126 and is coupled to the inner skirt 120 such that the flap 148 is in tension and biased to a closed state. More precisely, a first corner 154 and a second corner 156 of the second end 152 of the flap 148 is coupled to the inner skirt 120, as best seen in FIG. 5. Each flap 148 may be formed of a flexible material such as, but not limited to silicone, chronoprene, urethane, polyester, nylon, expanded polytetrafluoroethylene (ePTFE), natural tissue (e.g. porcine, equine, or bovine pericardium), or other materials suitable for the purposes described herein. The first end 150 of each flap 148 may be coupled to the outer wrap 122 by methods such as, but not limited to sutures, laser or ultrasonic welding, or outer suitable methods. While described as a separate component, each flap 148 may alternatively be formed as an integral portion of the inflow end 136 of the outer wrap 122 extending from the inflow end 132 and folded during assembly to form the flap 148. The first corner 154 and the second corner 156 of the flap 148 may be coupled to the inner skirt 120 122 by methods such as, but not limited to sutures, laser or ultrasonic welding, or outer suitable methods.

Figure 6:
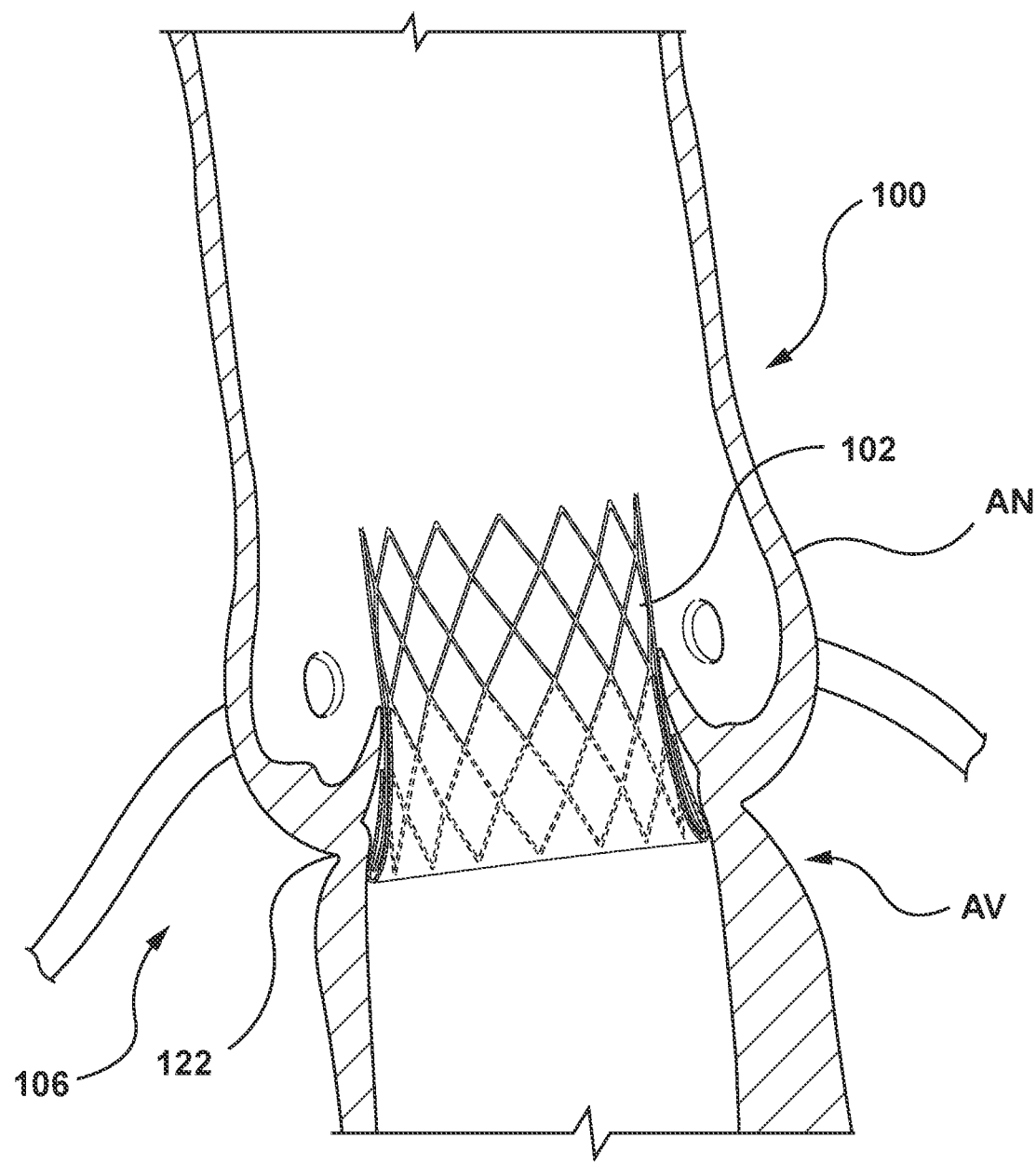
FIG. 6 is a schematic sectional illustration of the prosthesis of FIG. 1 implanted within an annulus of a native aortic valve.
Figure 7:
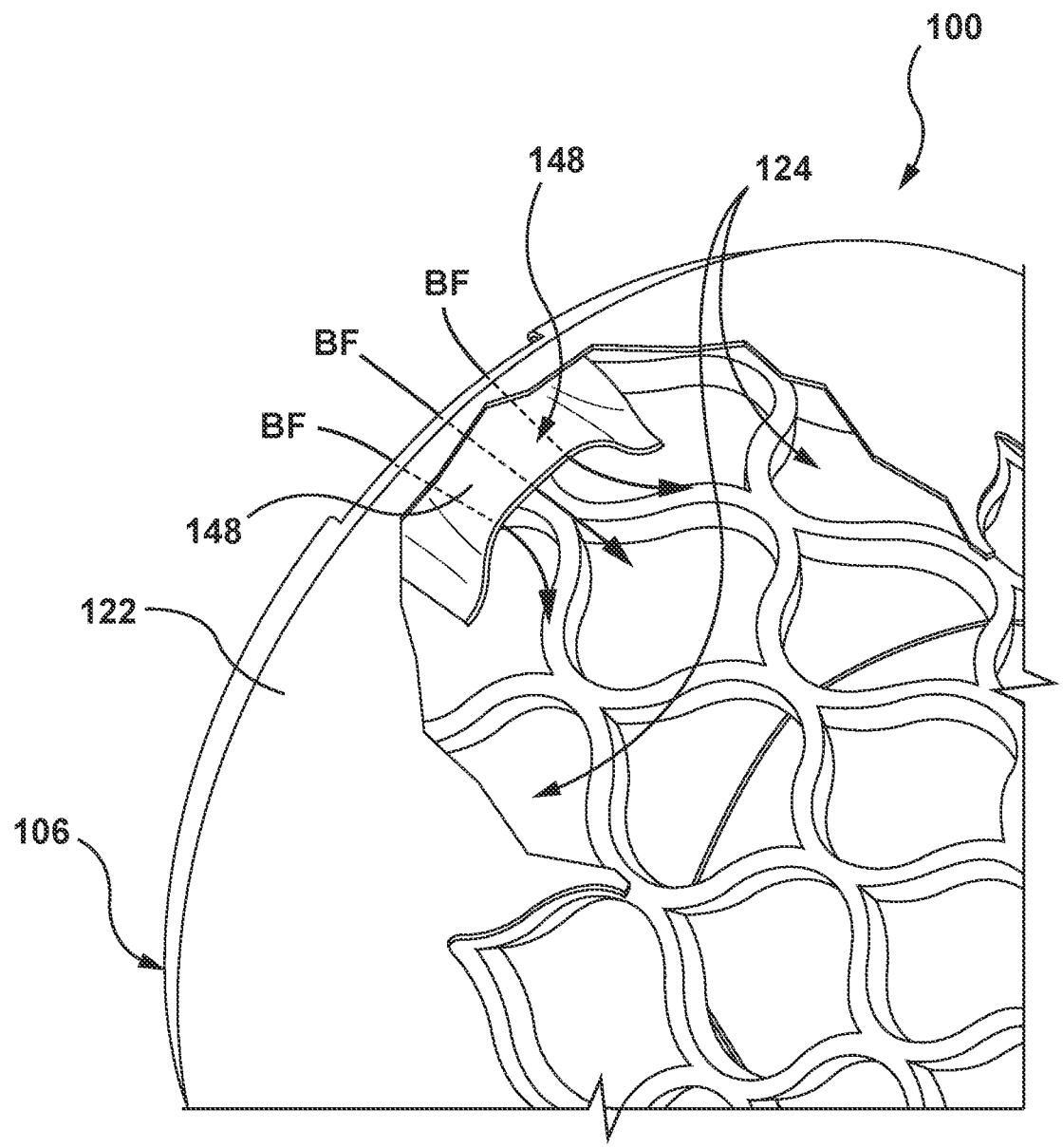
FIG. 7 is a perspective illustration of the inflow portion of the prosthesis of FIG. 1, with the one-way valve of the anti-PVL component open.

With an understanding of the components of the prosthesis 100, is now possible to describe their interaction to seal the prosthesis 100 at a desired treatment location, such as a native aortic valve, as shown in FIG. 6. The prosthesis 100 is delivered and deployed at the desired treatment location using established procedures. "Deployed" as used herein means that the prosthesis 100 is located at an annulus AN of a desired native heart valve, such as the native aortic valve AV, and the tubular stent 102 is in the radially expanded configuration. However, in some patients, the radial expansion of the tubular stent 102 may not fully conform to the shape of the wall of the native heart valve. Accordingly, and as best shown in FIG. 7, once the prosthesis 100 is deployed at the desired treatment location, during systole, blood is forced through the valve component 104 (not visible in FIGS. 7-8) of the prosthesis 100. The higher pressure on the inner surface of the flap 148 relative to the pressure on the outer surface of the flap 148 within the cavity 124, forces the flap 148 outward. More particularly, the portions of the flap 148 between the inflow end 132 of the outer wrap 122 and the first corner 154, between the first corner 154 and the second corner 156, and between the second corner 156 and the inflow end 132 of the outer wrap 122 are forced outward, thereby creating a gaps between the inner surface of the flap 148 and the outer surface of the stent 102 at those locations. These caps permit blood BF to flow into the cavity 124 of the anti-PVL component 106. Blood BF entering the cavity 124 distends or expands the outer wrap 122 radially outward to the radially expanded state. As the wrap 122 distends or expands to the radially expanded state, the outer wrap 122 of the anti-PVL component 106 conforms to or fills in gaps in the shape of the native anatomy, thereby preventing blood flow between the prosthesis 100 and the wall of the native aortic valve AV, as shown in FIG. 6. It will be understood that once pressure inside the cavity 124 is equal to the pressure outside the cavity 124, blood will cease to flow into the cavity 124.

Figure 8:
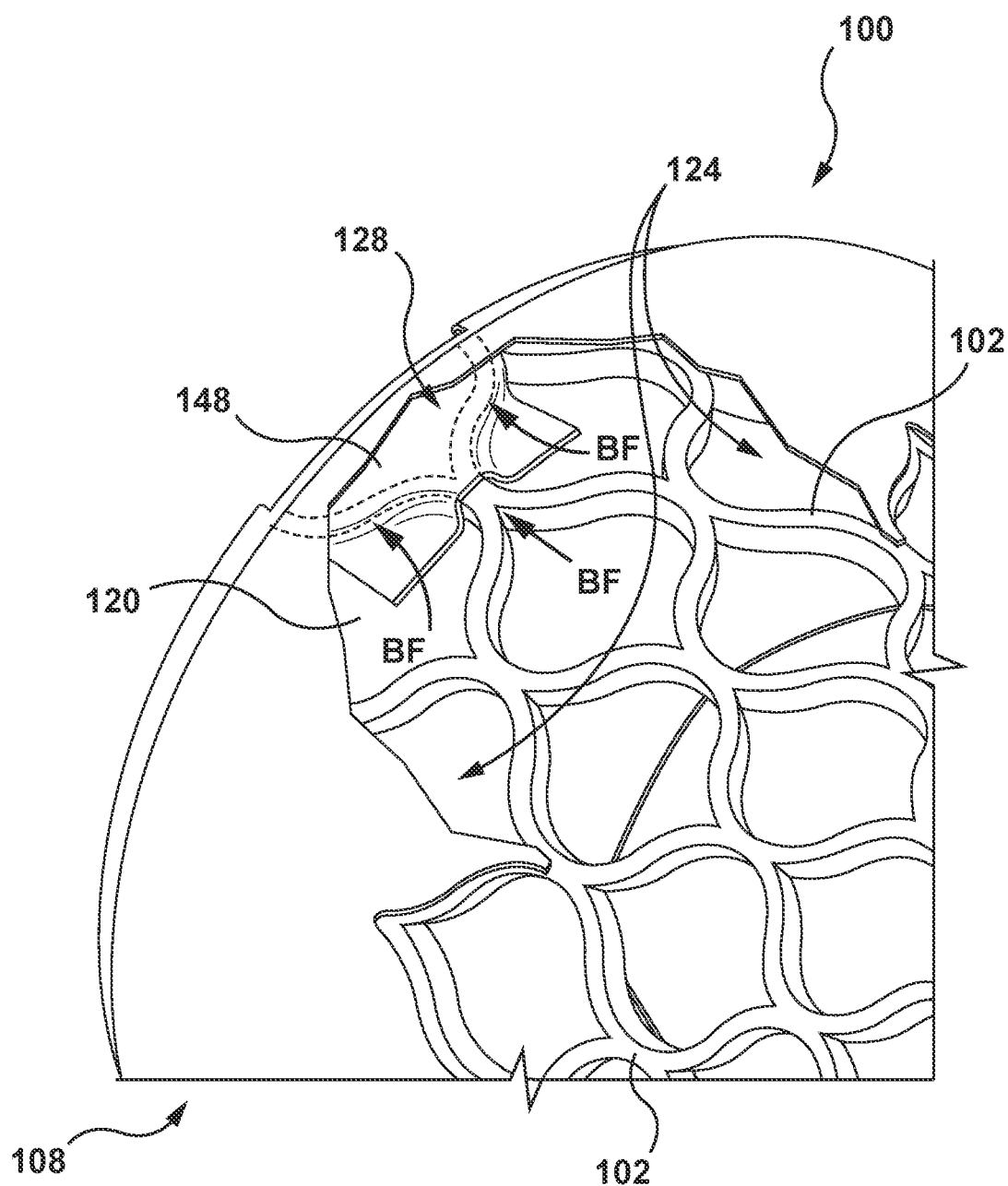
FIG. 8 is a perspective illustration of the inflow portion of the prosthesis of FIG. 1, with the one-way valve of the anti-PVL component closed.

When the heart relaxes and the pressure outside the cavity 124 decreases, the valve component 104 (not visible in FIGS. 7-8) of the prosthesis 100 closes to prevent regurgitation or backflow upstream and the relatively greater pressure within the cavity 124 forces the flap 148 radially inward against the stent 102 and the outer surface of the inner skirt 120. Movement of the flap 148 radially inward closes the flap 148 of the valve 128 and prevents blood BF from flowing out of the cavity 124, as shown in FIG. 8.

Moreover, once the cavity 124 is filled with blood BF, the cavity 124 becomes dynamically stable to minimize movement of the prosthesis 100 at the desired treatment location and promote healing and ingrowth. Even further, over time, the blood trapped within the cavity 124 will clot to form a permanent seal between the prosthesis 100 and the wall of the native anatomy. In other words, due to the one way valves 128, the cavity 124 will not pulse between a larger and smaller radial dimension. Instead, the cavity 124 will fill to radially expanded, and then stay radially expanded.

While described herein with three (3) openings 126 and three corresponding valves 128 at the inflow end 108 of the stent 102, this is not meant to be limiting, and it will be understood that more or fewer openings 126 and corresponding valves 128 may be utilized. Moreover, it will be understood that the valves 128 may be disposed at other locations of the anti-PVL component, some non-limiting examples of which are described below.

Figure 9A:
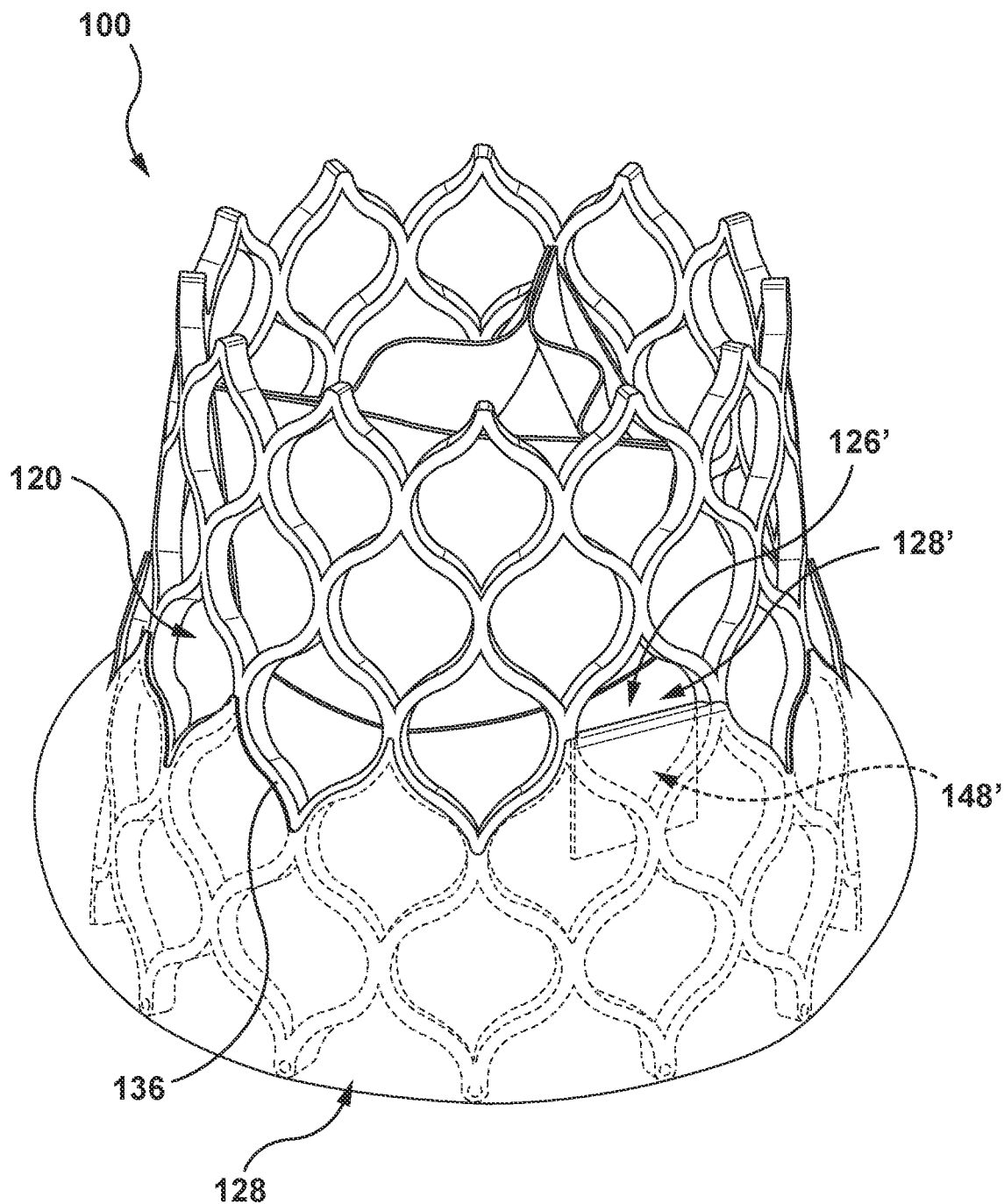
FIG. 9A is a perspective illustration of the inflow portion of the prosthesis of FIG. 1, with one-way valves disposed at the downstream end of the anti-PVL component and the valve component omitted for clarity.
Figure 9B:
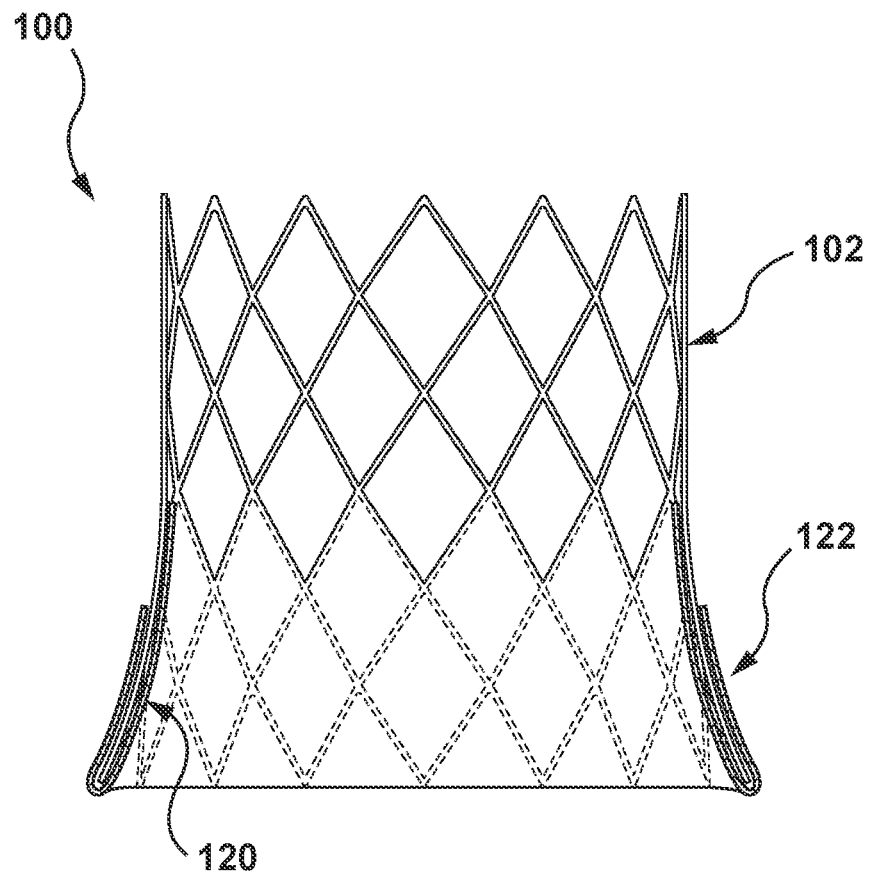
FIG. 9B is a side illustration of the prosthesis of FIG. 9A.

In an alternate configuration, the plurality of valves 128' are disposed at the downstream ends 132, 138 of the inner skirt 120 and the outer wrap 122 respectively, as shown in FIGS. 9A and 9B. In an embodiment, the valves 128' can be formed similar to the valves 128, except at the downstream end of inner skirt 120 and outer wrap 122. In another embodiment, the inner skirt 120 and the outer wrap 132 are a single piece that wraps around the upstream end of the stent 102, as shown in FIG. 9B. The downstream end 132 of the inner skirt 120 is coupled to the inner surface of the stent 102 and the downstream end 138 of the outer wrap 122 is coupled to the stent 102. An opening 126' is formed where a portion of the inner skirt 120 is not coupled to the inner surface of the stent 102. Accordingly, each opening 126' is disposed at the downstream ends 132, 138 of the inner skirt 120 and the outer wrap 122, respectively, between the inner skirt 120 and the outer wrap 122. Each opening 126' is configured to allow blood flow to the corresponding valve 128' of the anti-PVL component 106.

Each valve 128' includes a flap 148'. Each flap 148' includes a first end 150' coupled to the downstream end 138 of the outer wrap 122 at the opening 126' and a second end 152'. As explained above, each flap 148' may be integral with the outer wrap 122 and folded back in an upstream direct and tucked between the outer wrap 122 and the stent 102. A portion of each flap 148' spaced from the first end 150', in this example a first corner 154' and a second corner 156' of the second end 152 of each flap 148', and is coupled to the inner skirt 120.

For valves 128' disposed at the downstream ends 132, 138 of the inner skirt 120 and the outer wrap 122, respectively, and with the prosthesis 100 delivered and deployed at the desired treatment location, as the heart relaxes, pressure at the inflow end 108 of the tubular stent 102 decreases. The relatively higher pressure at the downstream ends 132, 138 of the inner skirt 120 and the outer wrap 122, respectively, and more specifically on the inner surface of each flap 148' of each one-way valve 128', forces each flap 148' outward towards the inner surface of the outer wrap 122, thereby creating the gaps described above with respect to the embodiment of FIGS. 1-8. The corresponding valve 128' is thusly opened to permit blood flow into the cavity 124 of the anti-PVL component 106. The outer wrap 122 expands radially outward to the radially expanded state as blood enters the cavity 124, and as the outer wrap 122 radially expands, the outer wrap 122 conforms to the shape of the native anatomy to prevent blood flow between the prosthesis 100 and the wall of the native valve. When the heart contracts, blood is forced through the prosthesis 100 and the pressure outside the cavity 124 decreases. The relatively greater pressure within the cavity 124 forces each flap 148' radially inward against the tubular stent 102 and the outer surface of the inner skirt 120. Each flap 148' forced radially outward closes the corresponding valve 128' and prevents blood from flowing out of the cavity 124.

Figure 10:
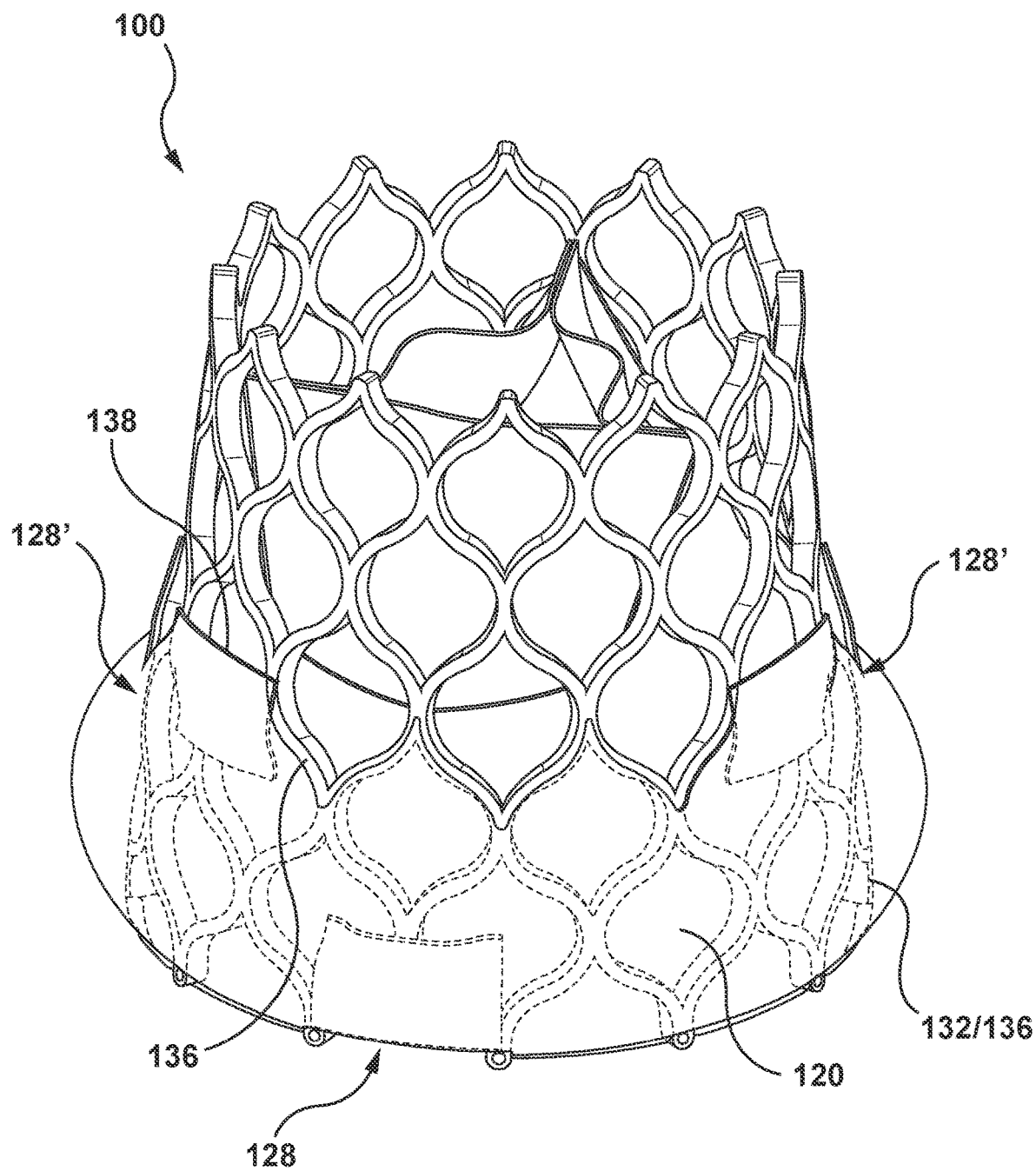
FIG. 10 is a perspective illustration of the prosthesis of FIG. 1, with one-way valves disposed at both the inflow and downstream ends of the anti-PVL component.

While the plurality of valves 128, 128' have been described as disposed at either the inflow ends 130, 136 or the downstream ends 132, 138 of the inner skirt 120 and the outer wrap 122 respectively, this is not meant to be limiting and the valves 128, 128' may be utilized at both the inflow ends 130, 136 and the downstream ends 132, 138 of the inner skirt 120 and the outer wrap 122 respectively, in any combination, as shown in FIG. 10. In particular, FIG. 10 shows the prosthesis 100 with three (3) one-way valves 128 at the inflow ends 130, 136 of the inner skirt 120 and the outer wrap 122 and three (3) one-way valves 128' at the downstream ends 132, 138 of the inner skirt 120 and the outer wrap 122. FIG. 10 does not show all of the valves 128, 128' because some are hidden from view as being on the side of the prosthesis 100 that is not visible. Also, FIG. 10 shows the prosthesis 100 with the outer wrap 122 removed for clarity. In the embodiment of FIG. 10, the valves 128 are evenly distributed around the circumference of the inflow end of the prosthesis 100 and the valves 128' are evenly distributed around the downstream ends 132, 138 of the inner skirt 120 and outer wrap 122. However, this is not meant be limiting and any number of valves may be used and they may or may not be evenly distributed around the circumference. Also, FIG. 10 shows each inflow valve 128 circumferentially offset from each downstream valve 128'. However, this is not meant to be limiting and other arrangements by be utilized, such as the valves 128, 128' circumferentially aligned.

Figure 11:
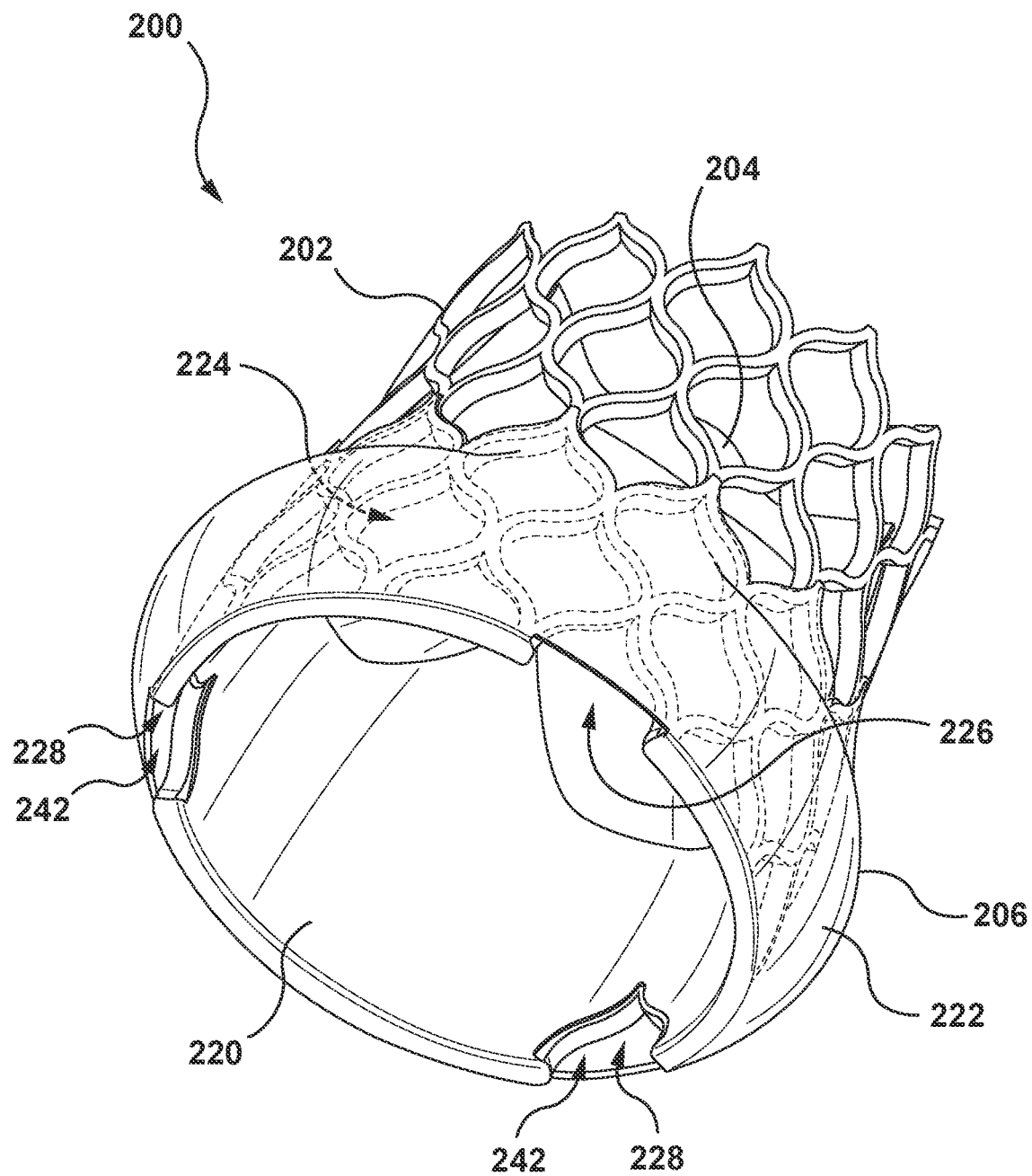
FIG. 11 is a perspective illustration of a prosthesis with an anti-PVL component according to another embodiment hereof.

A transcatheter valve prosthesis 200 according to another embodiment hereof is shown in FIG. 11. The transcatheter valve prosthesis 200 (hereafter referred to as prosthesis 200 for simplicity) includes a generally tubular stent 202, a prosthetic valve component 204 (hereafter referred to as valve component 204 for simplicity), and an anti-paravalvular leakage component 206 (hereafter referred to as anti-PVL component 206 for simplicity). The anti-PVL component 206 includes an inner skirt 220, an outer wrap 222, a cavity 224 (not visible in FIG. 11 but visible in FIG. 12), a plurality of openings 226, and a corresponding plurality of one-way duckbill valves 228. The stent 202, the valve component 204, the anti-PVL component 206, the inner skirt 220, the outer wrap 222, the cavity 224 and the plurality of openings 226 are similar to the stent 102, the valve component 104, the anti-PVL component 106, the inner skirt 120, the outer wrap 122, the cavity 124 and the plurality of openings 126 of the prosthesis 100. Therefore, construction and alternatives of the tubular stent 202, the valve component 204, the anti-PVL component 206, the inner skirt 220, the outer wrap 222, the cavity 224, and the plurality of openings 226 will not be repeated. However, the prosthesis 200 differs from the prosthesis 100 in that the prosthesis 200 includes a plurality of one-way duckbill valves 228 at the plurality of openings 226.

As shown in FIG. 11, the anti-PVL component 206 includes the plurality of openings 226 are disposed between the inner skirt 220 and the corresponding plurality of valves 228. While shown as three (3) openings 226 spaced equally at an inflow end 230 of the inner skirt 220 and an inflow end 232 of the outer wrap 222, it will be understood that more or fewer openings 126 may be utilized. Additionally, the plurality of openings 226 may be disposed with any suitable spacing at the inflow ends 230, 232 and/or the downstream ends 236, 236 of the inner skirt 220 and the outer wrap 222.

Figure 12:
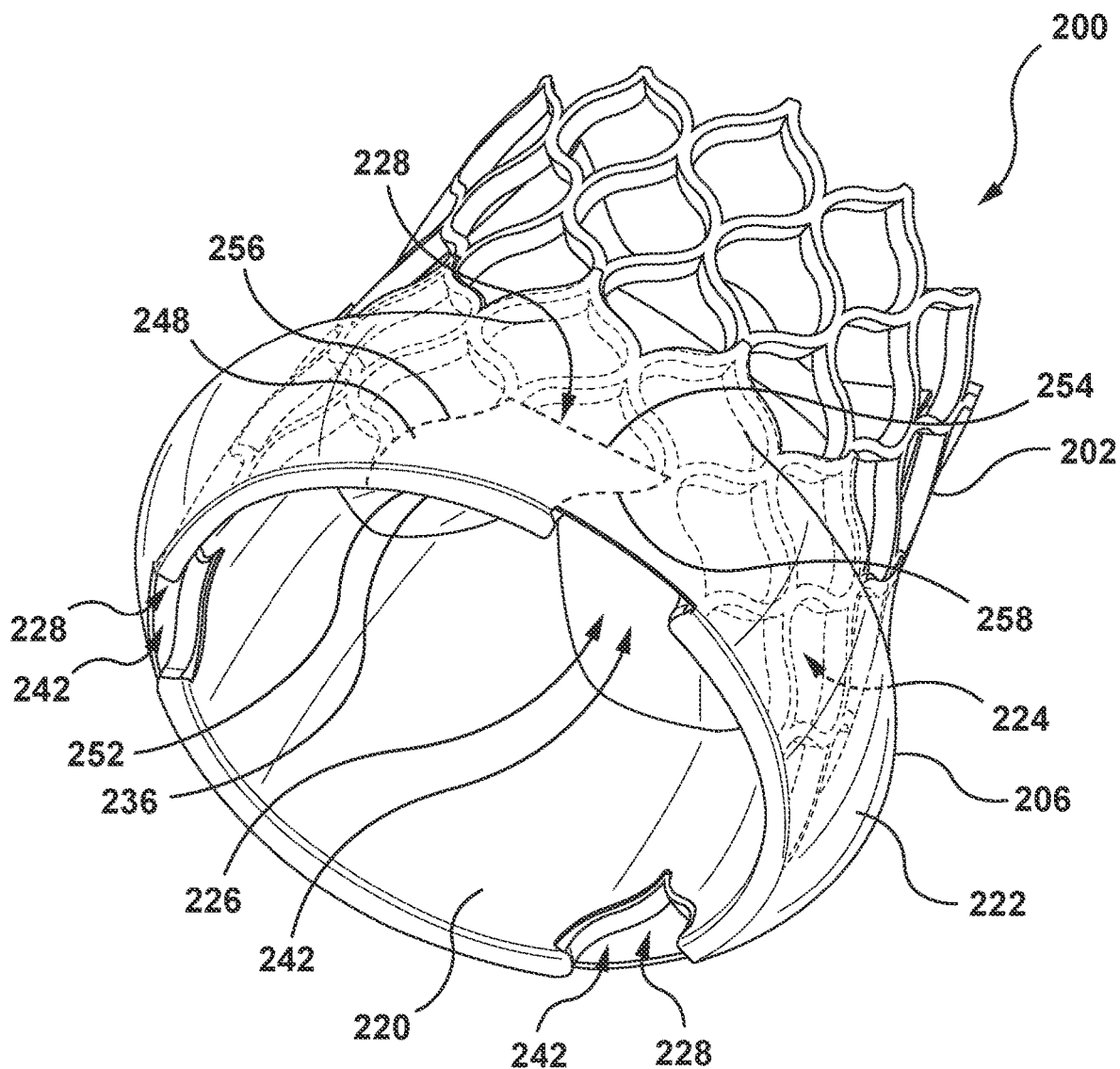
FIG. 12 is another perspective illustration of the prosthesis of FIG. 11, with an inner flap of a duckbill valve shown in phantom.
Figure 12A:
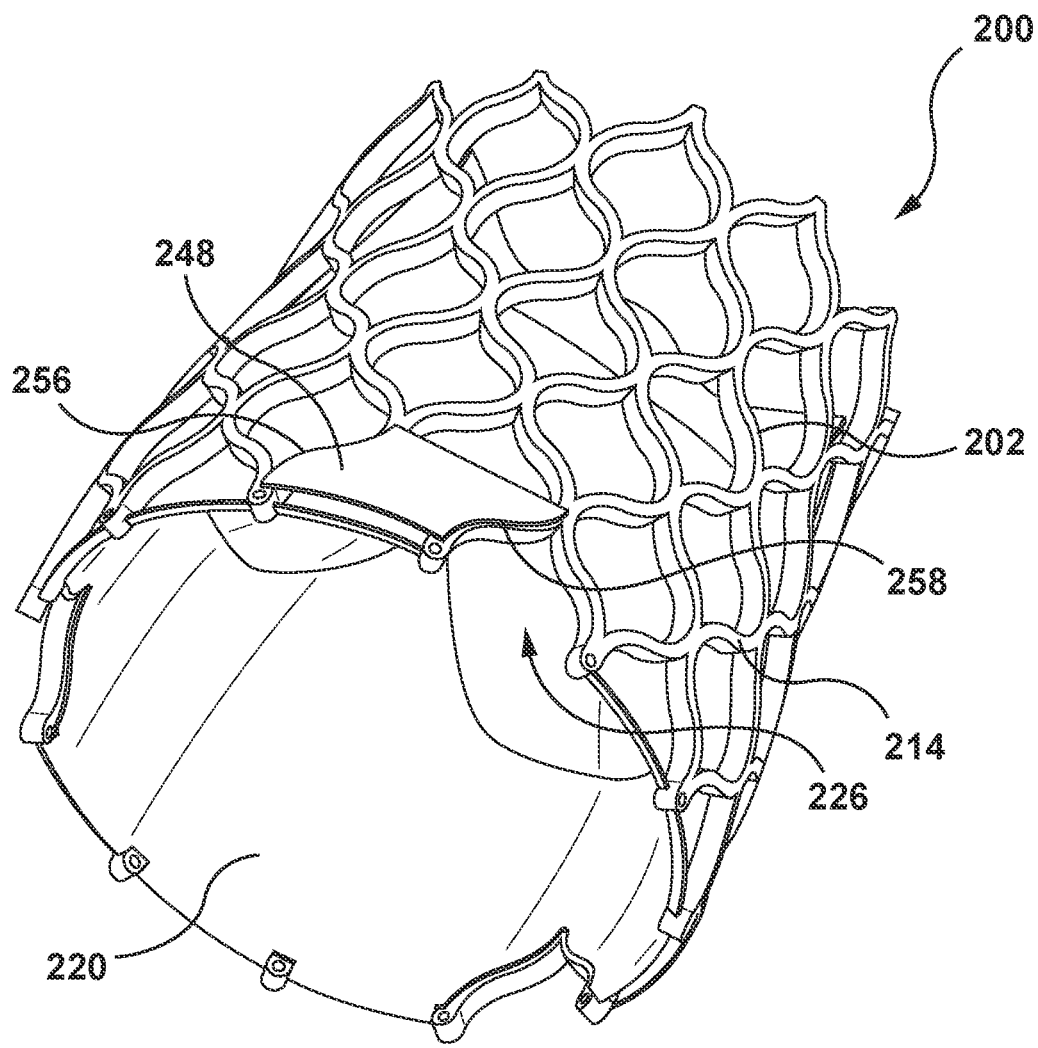
FIG. 12A is another perspective illustration of the prosthesis of FIG. 11, with the outer wrap removed for clarity to show the inner flap of the duckbill valve.
Figure 13:
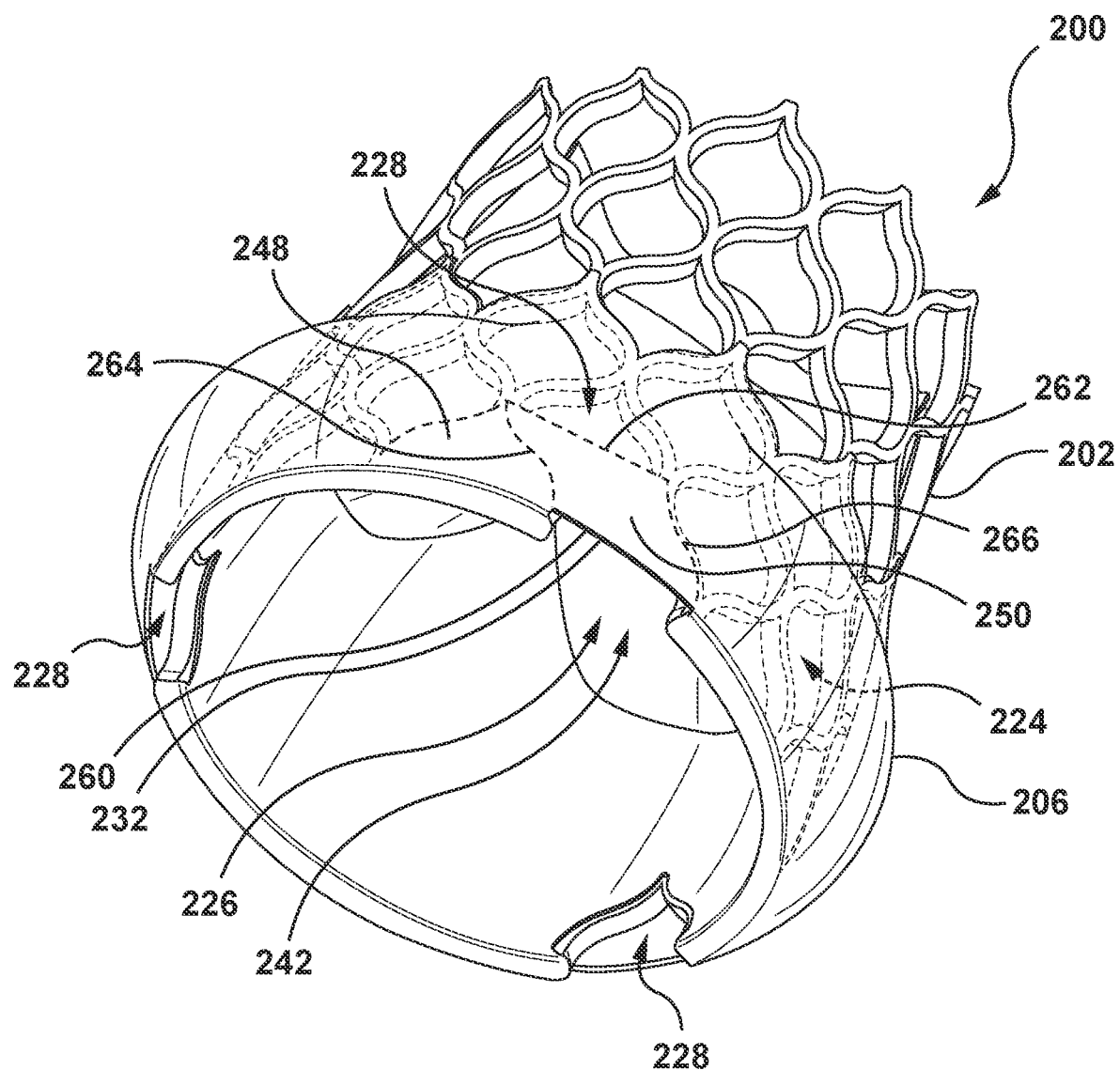
FIG. 13 is another perspective illustration of the prosthesis of FIG. 11, with an outer flap of the duckbill valve shown in phantom.
Figure 13A:
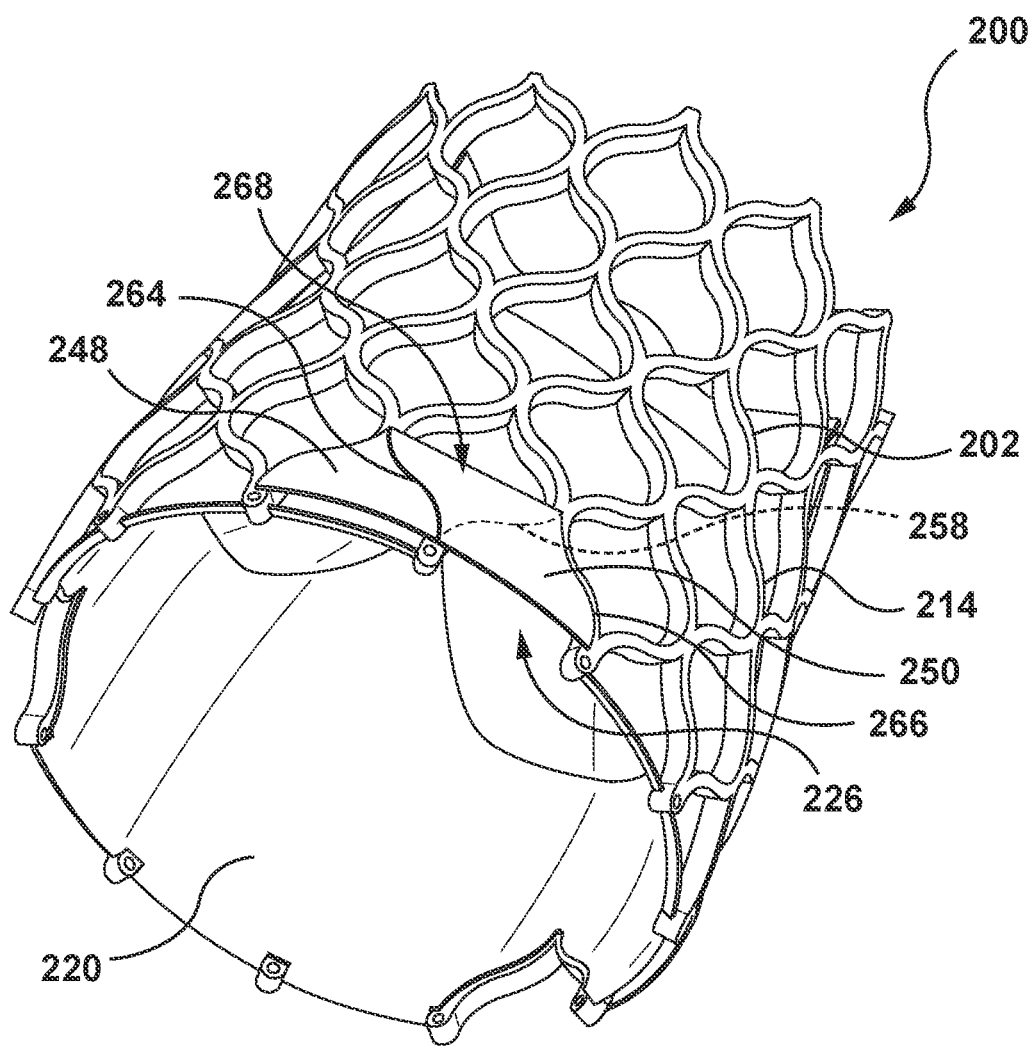
FIG. 13A is another a perspective illustration of the prosthesis of FIG. 11, with the outer wrap removed for clarity to show the outer flap of the duckbill valve.

Referring next to FIGS. 12 and 12A, each one-way duckbill valve 228 of the plurality of one-way duckbill valves 228 (hereafter referred to as duckbill valve(s) 228 for simplicity) includes an inner flap 248, as best shown in FIG. 12A, and an outer flap 250 as best shown in FIG. 13A. The inner flap 248 and the corresponding outer flap 250 of each duckbill valve 228 are configured to open to allow blood flow into the cavity 224 of the anti-PVL component 206. The inner flap 248 and the corresponding outer flap 250 of each duckbill valve 228 are further configured to close to prevent blood flow from out of the cavity 224. The inner and outer flaps 248, 250 of each duckbill valve 228 may be formed of a flexible material, non-limiting examples of which include silicone, chronoprene, urethane, polyester, nylon, expanded polytetrafluoroethylene (ePTFE), natural tissue (e.g. porcine, equine, or bovine pericardium), or other materials suitable for the purposes described herein.

The inner flap 248 of each duckbill valve 228 is disposed adjacent the corresponding opening 226, between an outer surface of the stent 202 and an inner surface of the outer wrap 222, as shown in FIGS. 12 and 12A. Each inner flap 248 includes a first (longitudinal) end 252 coupled to an inflow end 236 of the outer wrap 222, adjacent a cut-out portion 242 of the inner skirt 220, and an opposing second (longitudinal) end 254. Each inner flap 248 further includes a first (lateral) edge 256 and an opposing second (lateral) edge 258, each attached along a strut 214 of the stent 202. As can be seen in FIGS. 12 and 12A, the inner flap 248 is angled in a first direction towards the opening 226. The first end 252 may be coupled to the outer wrap 222 and the first edge 256 and the second edge 258 may be coupled to the struts 214 of the stent 202 by methods such as, but not limited to sutures, laser or ultrasonic welding, or outer suitable methods. While described as a separate component, each inner flap 248 may alternately be an integral portion of the inner skirt 220, extending from the inflow end 230 of the inner skirt 220 folded to form the inner flap 248 during assembly.

The outer flap 250 of each duckbill valve 228 is disposed at the corresponding opening 226, between the outer surface of the tubular stent 202 and the inner surface of the outer wrap 222, as shown in FIGS. 13 and 13A. Each outer flap 250 includes a first (longitudinal) end 260 coupled to an inflow end 236 of the outer wrap 222 at the cut-out portion 242 of the inner skirt 220 and an opposing second (longitudinal) end 262. Each outer flap 250 further includes a first (lateral) edge 264 and a second (lateral) edge 266 each coupled to corresponding struts 214 of the stent 202. As can be seen in FIG. 13 by the dashed line, the second edge 258 of the inner flap 248 is attached to the corresponding strut 214 of the stent 202 under the outer flap 250. Further, the outer flap 250 is angled towards the inner flap 248 such that the outer flap 250 overlaps the inner flap 248. In the embodiment shown, the overlap is in an overlap region 268 defined by the first edge 264 of the outer flap 250, the second edge 258 of the inner flap 248, and the second ends 254, 262 of the inner and outer flaps 248, 250. Further, the second ends 254, 262 of the inner and outer flaps 248, 250 are not attached to each other so as to permit blood flow therethrough, as explained in more detail below. The first end 260 may be coupled to the outer wrap 222 and the first edge 264 and the second edge 266 may be coupled to the corresponding struts 214 of the stent 202 by methods such as, but not limited to sutures, laser or ultrasonic welding, or outer suitable methods. Although each outer flap 250 is described as a separate component, alternatively, each outer flap 250 may be an extension of the inflow end 232 of the outer wrap 222 folded to form the outer flap 250 during assembly.

Figure 14:
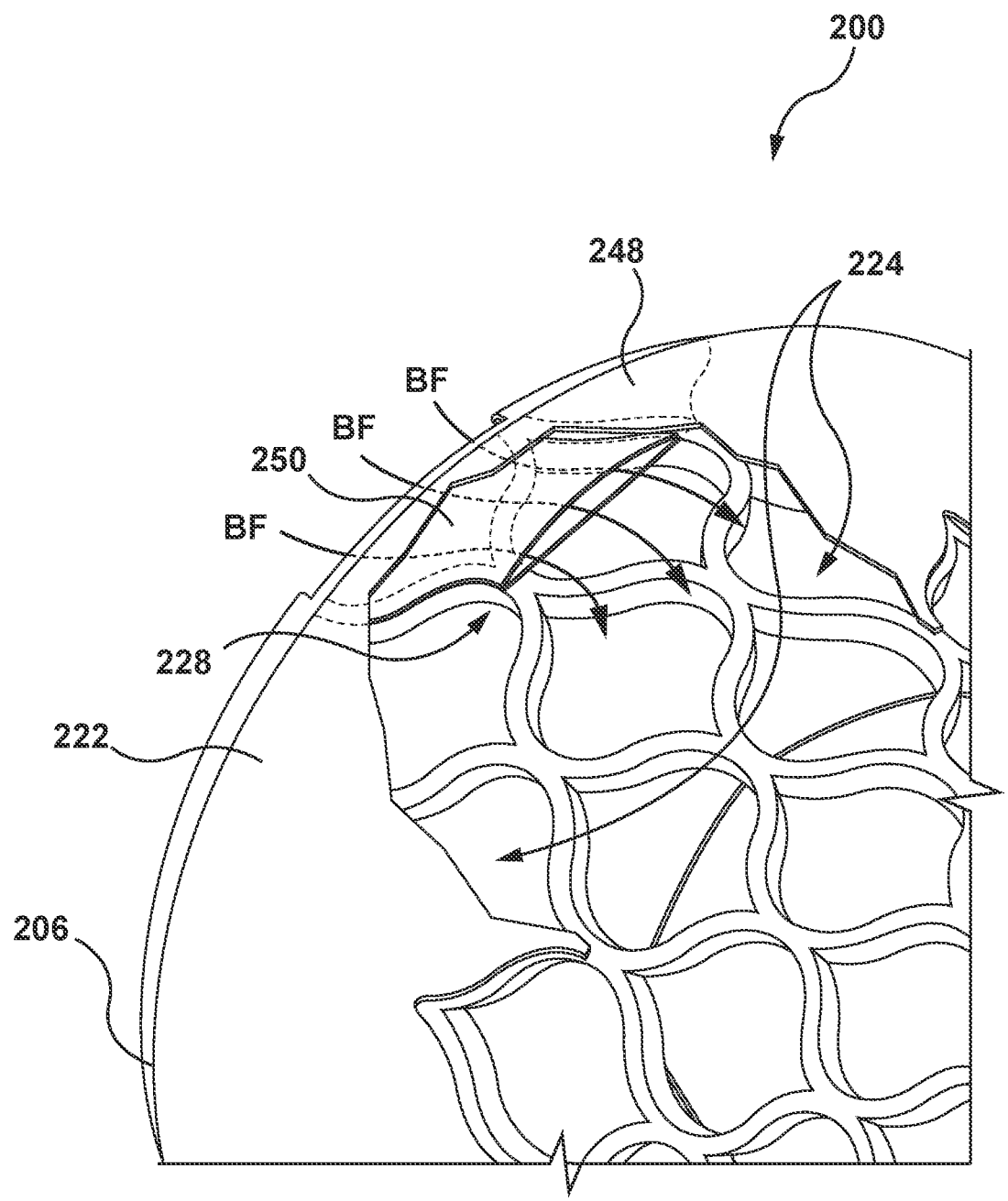
FIG. 14 is a perspective illustration of the inflow portion of the prosthesis of FIG. 11, with the duckbill valve opened.
Figure 15:
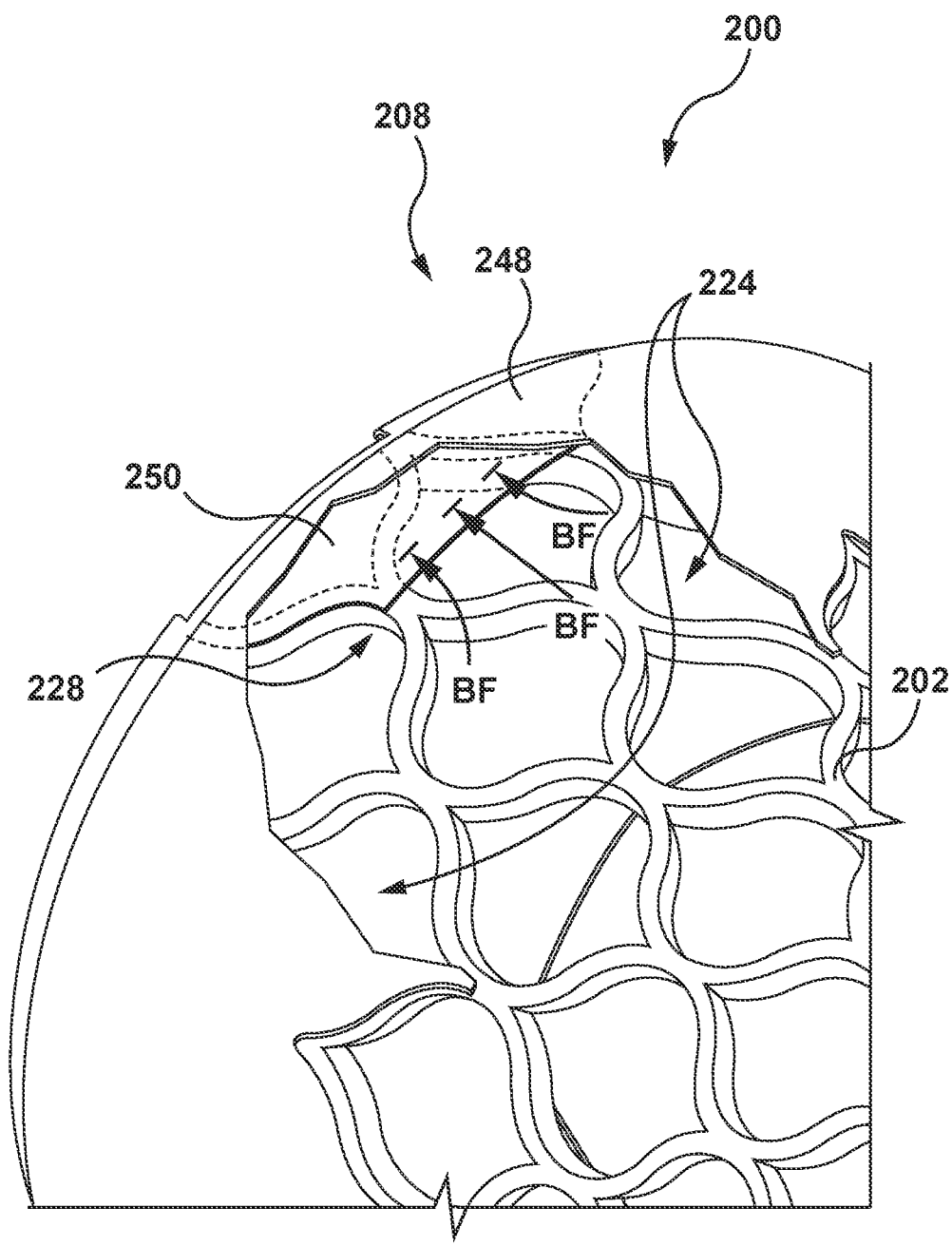
FIG. 15 is a perspective illustration of the inflow portion of the prosthesis of FIG. 11, with the duckbill valve is closed.

It is now possible to describe interaction of the components of the prosthesis 200 to seal the prosthesis 200 at a desired treatment location. The prosthesis 200 is delivered and deployed at the desired treatment location using established procedures. As shown in FIG. 14, once the prosthesis 200 is deployed at the desired treatment location and during systole, the heart contracts and forces blood through the valve component 204 (not visible in FIGS. 14-15) of the prosthesis 200. Pressure on an inner surface of the outer flap 250 forces each outer flap 250 outward, thereby opening opens the duckbill valve. The open duckbill valve 228 permits blood BF to flow between the corresponding inner and outer flaps 248, 250 and into the cavity 224 of the anti-PVL component 206. More particularly, blood flows into the corresponding opening 226, over the corresponding strut 214 and second edge 258 of the inner flap 248, between the inner flap 248 and the outer flap 250 in the overlap region 268, and into the cavity 224 between the separated second ends 254, 262 of the inner and outer flaps 248, 250, as shown in FIG. 14. Blood fills the cavity 224 and distends the outer wrap 222 radially outward to the radially expanded state. The outer wrap 222 conforms to the shape of the native anatomy and prevents blood flow between the prosthesis 200 and the wall of the native heart valve. With reference next to FIG. 15, when the heart relaxes, the pressure decreases outside the cavity 224 and the relatively greater pressure inside the cavity 224 closes the corresponding duckbill valve 228. More specifically, pressure on an outer surface of the outer flap 250 forces the outer flap 250 radially inward against the stent 202, the outer surface of the inner skirt 220, and an outer surface of the inner flap 248 to close the corresponding duckbill valve 228. The closed duckbill valve 228 prevents blood BF from flowing out of the cavity 224.

The cavity 224 becomes dynamically stable when filled with blood BF. This stability promotes healing and ingrowth of the prosthesis 200 at the desired treatment location. Over time, the blood trapped within the cavity 224 will clot to form a permanent seal between the prosthesis 200 and the wall of the native anatomy. In other words, due to the one way valves 128, the cavity 124 will not pulse between a larger and smaller radial dimension. Instead, the cavity 124 will fill to radially expanded, and then stay radially expanded.

While described herein with three (3) openings 226 and three corresponding duckbill valves 228 at the inflow ends 230, 236 of the inner skirt 220 and the outer wrap 222, it will be understood that more or fewer openings 226 and corresponding duckbill valves 228 may be utilized. Further, the plurality of duckbill valves 228 may be located at the inflow ends 230, 236 and/or the downstream ends 232, 238 of the inner skirt 220 and the outer wrap 222 in any combination. When the plurality of duckbill valves are disposed at the downstream ends 232, 238, the downstream end 232 of the inner skirt 220 is coupled to the inner surface of the tubular stent 202 and the downstream end 238 of the outer wrap 222 is coupled to the outer surface of the tubular stent 202 along a common line and the plurality of openings are formed where a portion of the inner skirt 220 is not attached to the inner surface of the stent 202, as described above with respect to FIG. 9.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:
1. A transcatheter valve prosthesis comprising:
 a stent having a radially compressed configuration for delivery within a vasculature and a radially expanded configuration for deployment within a native heart valve;
 a prosthetic valve component disposed within and secured to the stent; and
 an anti-paravalvular leakage component coupled to the stent, the anti-paravalvular leakage component including:
  an inner skirt formed of a flexible material, the inner skirt encircling an inner surface of the stent and having an inflow end and an opposing downstream end;
  an outer wrap formed of a flexible material, the outer wrap being disposed around an outer surface of the stent and having an inflow end coupled to the inflow end of the inner skirt and an opposing downstream end;
  a cavity formed between an outer surface of the inner skirt and an inner surface of the outer wrap;
  an opening in fluid communication with the cavity, the opening disposed at the corresponding inflow ends of the inner skirt and the outer wrap and/or the corresponding downstream ends of the inner skirt and the outer wrap; and
  a one-way duckbill valve including an inner flap and an outer flap formed of a flexible material, one of the inner flap and the outer flap is disposed adjacent the opening, the inner and outer flaps disposed between the outer surface of the stent and the inner surface of the outer wrap, and the inner flap being attached to the stent.

2. The transcatheter valve prosthesis of claim 1, wherein the anti-paravalvular leakage component includes a plurality of openings and a corresponding plurality of one-way duckbill valves.

3. The transcatheter valve prosthesis of claim 1, wherein the inflow ends of the inner skirt and the outer wrap are generally circular, and wherein the opening is formed by a cut-out portion of the inflow end of the inner skirt being attached to the inner surface of a portion of the stent such that the cut-out portion of the inflow end of the inner skirt is downstream of the inflow end of the outer wrap.

4. The transcatheter valve prosthesis of claim 3, wherein the opening is defined by a portion of the stent at the cut-out portion of the inner skirt, the inflow end of the inner skirt at the cut-out portion, and the inner surface of the outer wrap at the cut-out portion of the inner skirt.

5. The transcatheter valve prosthesis of claim 4, wherein a first longitudinal end of the inner flap of the one-way duckbill valve is coupled to the inflow end of the outer wrap adjacent the cut-out portion of the inner skirt.

6. The transcatheter valve prosthesis of claim 5, wherein a first lateral edge of the inner flap is coupled to the stent and an opposing second lateral edge of the inner flap is coupled to the stent.

7. The transcatheter valve prosthesis of claim 4, wherein a first longitudinal end of the outer flap of the one-way duckbill valve is coupled to the inflow end of the outer wrap at the cut-out portion of the inner skirt.

8. The transcatheter valve prosthesis of claim 7, wherein a first lateral edge of the outer flap is coupled to the stent and an opposing second lateral edge of the inner flap is coupled to the stent.

9. The transcatheter valve prosthesis of claim 8, wherein the first lateral edge of the outer flap is coupled to the stent through the inner flap.

10. The transcatheter valve prosthesis of claim 1, wherein the downstream end of the inner skirt is coupled to the inner surface of the stent and the downstream end of the outer wrap is coupled to the outer surface of the stent such that the downstream ends of the inner skirt and the outer wrap are coupled to the stent along a common line, wherein the opening is formed where a portion of the inner skirt is not attached to the inner surface of the stent.

11. The transcatheter valve prosthesis of claim 1, wherein another of the outer flap and the inner flap is disposed at the opening.

12. The transcatheter valve prosthesis of claim 11, wherein the inner flap is disposed adjacent to the opening and the outer flap is disposed at the opening.

13. The transcatheter valve prosthesis of claim 12, wherein the inner flap is angled towards the opening from a downstream end to an upstream end of the inner flap, and wherein the outer flap is angled away from the opening from a downstream end to an upstream end of the outer flap.

14. The transcatheter valve prosthesis of claim 1, wherein the duckbill valve is configured to allow blood flow into the cavity between the inner flap and the outer flap.

15. The transcatheter valve prosthesis of claim 1, wherein the outer flap is attached to the stent and overlaps the inner flap.

* * * * *